United States Patent
Seeber et al.

(10) Patent No.: US 10,718,762 B2
(45) Date of Patent: Jul. 21, 2020

(54) CELLULAR BASED FRET ASSAY FOR THE DETERMINATION OF SIMULTANEOUS BINDING

(71) Applicant: Hoffmann-La Roche Inc., Little Falls, NJ (US)

(72) Inventors: Stefan Seeber, Sindelsdorf (DE); Jens Fischer, Weilheim in Oberbayern (DE); Georg Fertig, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 291 days.

(21) Appl. No.: 15/941,787

(22) Filed: Mar. 30, 2018

(65) Prior Publication Data

US 2018/0328920 A1 Nov. 15, 2018

Related U.S. Application Data

(63) Continuation of application No. PCT/EP2016/073186, filed on Sep. 29, 2016.

(30) Foreign Application Priority Data

Oct. 2, 2015 (EP) .................... 15188065

(51) Int. Cl.
*G01N 33/542* (2006.01)
*G01N 33/544* (2006.01)

(52) U.S. Cl.
CPC ......... *G01N 33/542* (2013.01); *G01N 33/544* (2013.01)

(58) Field of Classification Search
None
See application file for complete search history.

(56) References Cited

U.S. PATENT DOCUMENTS

| 2006/0165685 A1 | 7/2006 | Kreysch et al. |
| 2010/0190266 A1 | 7/2010 | Sakita et al. |
| 2014/0242611 A1 | 8/2014 | Bazin et al. |
| 2015/0024410 A1 | 1/2015 | Jaga et al. |
| 2015/0044690 A1 | 2/2015 | Nakada et al. |
| 2015/0090936 A1 | 4/2015 | Hu et al. |

(Continued)

FOREIGN PATENT DOCUMENTS

| WO | 02/02773 A2 | 10/2002 |
| WO | 02/02773 A3 | 10/2003 |
| WO | 2007/062466 A1 | 7/2007 |

(Continued)

OTHER PUBLICATIONS

Beechem et al., "Global analysis of biochemical and biophysical data." Methods in Enzymology 210:37-54 ( 1992).

(Continued)

*Primary Examiner* — Rebecca M Giere
(74) *Attorney, Agent, or Firm* — Genentech, Inc.; Jonathan P. Aumais

(57) ABSTRACT

Herein is reported a method for the determination of the simultaneous binding of a bispecific antibody to a first and a second antigen comprising the steps of a) incubating a cell expressing cell-membrane bound FRET-donor-tagged first antigen and FRET-acceptor-tagged second antigen with the bispecific antibody, and b) determining the simultaneous binding of the bispecific antibody by determining the energy transfer from the FRET-donor to the FRET-acceptor.

8 Claims, 9 Drawing Sheets

Specification includes a Sequence Listing.

(56) References Cited

U.S. PATENT DOCUMENTS

2015/0204847 A1     7/2015     Thomas et al.

FOREIGN PATENT DOCUMENTS

WO     2013/113663     8/2013
WO     2014/055784     10/2014

OTHER PUBLICATIONS

Dong et al., "Time-resolved FRET reveals the structural mechanism of SERCA-PLB regulation" Biochemical and Biophysical Research Communications 449:196-201 ( 2014).

Gakamsky et al., "Use of fluorescence lifetime technology to provide efficient protection from false hits in screening applications" Analytical Biochemistry 409:89-97 ( 2011).

Gribbon et al., "Fluorescence readouts in HTS: no gain without pain?" Drug Discovery Today Yes 8:1035-43 ( 2003).

Isenberg et al., "The Analysis of Fluorescence Decay by a Method of Moments" Biophysical Journal 9:1337-1350 ( 1969).

ISR for PCT/EP2016/073186 (dated Nov. 25, 2016), pp. 6 (dated Dec. 9, 2016).

Jameson et al., "Investigations of protein-protein interactions using time-resolved fluorescence and phasors" Methods 59:278-286 (2013).

Knutson, et al., "Simultaneous analysis of multiple fluorescence decay curves: A global approach" Chemical Physics Letters 102:501-507 ( 1983).

Lebakken et al., "A fluorescence lifetime based binding assay to characterize kinase inhibitors" Journal of Biomolecular Screening 12(6):828-841 ( 2007).

Maltman et al., "9-Aminoacridine peptide derivatives as versatile reporter systems for use in fluorescence lifetime assays" Chemical communications (Cambridge, England) 46(37):6929-31 ( 2010).

Moger et al., "The Application of Fluorescence Lifetime Readouts in High-Throughput Screening" Journal of Biomolecular Screening 11:765-772 ( 2006).

Muretta et al., "High-performance time-resolved fluorescence by direct waveform recording." Rev. Sci. Instrum 81:103101-8 ( 2010).

Paterson et al., "A fluorescence lifetime-based assay for serine and threonine kinases that is suitable for high-throughput screeing" Analytical Biochemistry 402:54-64 ( 2010).

Thorne et al., "Apparent activity in high-throughput screening: origins of compound-dependent assay interference" Current Opinion in Chemical Biology 14:315-324 ( 2010).

Written Opinion for PCT/EP2016/073186, pp. 4 (dated Dec. 9, 2016).

Mallender et al., "Inter-Active-Site Distance and Solution Dynamics of a Bivalent-Bispecific Single-Chain Antibody Molecule" Biochemistry 33(33):10100-10108 (Apr. 25, 1994).

Shen et al., "Construction and expression of anti-B7-1 /B7-2-BsAb for feature analysis of its binding with antigen" Journal of Chinese Immune (English Abstract),:927-931 ( 2015).

SEQUENCE LISTING

```
<160> NUMBER OF SEQ ID NOS: 35

<210> SEQ ID NO 1
<211> LENGTH: 443
<212> TYPE: PRT
<213> ORGANISM: Artificial Sequence
<220> FEATURE:
<223> OTHER INFORMATION: heavy chain 1 of 1+1 PD1TIM3_0389 (based on
      chimeric PD1-0103 / Tim3-0028)

<400> SEQUENCE: 1

Lys Ile Val Leu Thr Gln Ser Pro Ala Ser Leu Pro Val Ser Leu Gly
1               5                   10                  15

Gln Arg Ala Thr Ile Ser Cys Arg Ala Ser Glu Ser Val Asp Thr Ser
            20                  25                  30

Asp Asn Ser Phe Ile His Trp Tyr Gln Gln Arg Pro Gly Gln Ser Pro
        35                  40                  45

Lys Leu Leu Ile Tyr Arg Ser Ser Thr Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Val Ala Thr Tyr Tyr Cys Gln Gln Asn Tyr
                85                  90                  95

Asp Val Pro Trp Thr Phe Gly Gly Gly Thr Lys Leu Glu Ile Lys Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190
```

```
Thr Tyr Ile Cys Asn Val Asn His Lys Pro Ser Asn Thr Lys Val Asp
            195                 200                 205

Lys Lys Val Glu Pro Lys Ser Cys Asp Lys Thr His Thr Cys Pro Pro
210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Ala Leu Gly Ala Pro Ile Glu Lys Thr Ile Ser Lys Ala Lys
                325                 330                 335

Gly Gln Pro Arg Glu Pro Gln Val Tyr Thr Leu Pro Pro Cys Arg Asp
            340                 345                 350

Glu Leu Thr Lys Asn Gln Val Ser Leu Trp Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
            435                 440

<210> SEQ ID NO 2
<211> LENGTH: 449
<212> TYPE: PRT
<213> ORGANISM: Artificial
<220> FEATURE:
<223> OTHER INFORMATION: heavy chain 2 of 1+1 PD1TIM3_0389

<400> SEQUENCE: 2

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Thr Thr
                20                  25                  30

Tyr Met His Trp Val Lys Gln Arg Pro Glu Gln Gly Leu Glu Trp Ile
            35                  40                  45

Gly Arg Ile Asp Pro Ala Asp Asp Asn Thr Lys Tyr Ala Pro Lys Phe
        50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Ala Ala Ile Tyr Tyr Cys
                85                  90                  95

Val Arg Asp Phe Gly Tyr Val Ala Trp Phe Ala Tyr Trp Gly Gln Gly
            100                 105                 110
```

Thr Leu Val Thr Phe Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Phe Thr Gln Lys Ser Leu Ser Leu Ser Pro Gly
        435                 440                 445

Lys

<210> SEQ ID NO 3
<211> LENGTH: 227
<212> TYPE: PRT
<213> ORGANISM: Artificial
<220> FEATURE:
<223> OTHER INFORMATION: light chain 1 of 1+1 PD1TIM3_0389

<400> SEQUENCE: 3

Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Ser Tyr

```
                20                  25                  30
Thr Met Ser Trp Val Arg Gln Thr Pro Glu Lys Arg Leu Asp Trp Val
             35                  40                  45
Ala Thr Ile Ser Gly Gly Arg Asp Ile Tyr Tyr Pro Asp Ser Val
 50                  55                  60
Lys Gly Arg Phe Thr Ile Ser Arg Asp Asn Ala Lys Asn Thr Leu Tyr
 65                  70                  75                  80
Leu Glu Met Ser Ser Leu Met Ser Glu Asp Thr Ala Leu Tyr Tyr Cys
                 85                  90                  95
Val Leu Leu Thr Gly Arg Val Tyr Phe Ala Leu Asp Ser Trp Gly Gln
             100                 105                 110
Gly Thr Ser Val Thr Val Ser Ser Ala Ser Val Ala Ala Pro Ser Val
             115                 120                 125
Phe Ile Phe Pro Pro Ser Asp Glu Gln Leu Lys Ser Gly Thr Ala Ser
             130                 135                 140
Val Val Cys Leu Leu Asn Asn Phe Tyr Pro Arg Glu Ala Lys Val Gln
145                 150                 155                 160
Trp Lys Val Asp Asn Ala Leu Gln Ser Gly Asn Ser Gln Glu Ser Val
                 165                 170                 175
Thr Glu Gln Asp Ser Lys Asp Ser Thr Tyr Ser Leu Ser Ser Thr Leu
             180                 185                 190
Thr Leu Ser Lys Ala Asp Tyr Glu Lys His Lys Val Tyr Ala Cys Glu
             195                 200                 205
Val Thr His Gln Gly Leu Ser Ser Pro Val Thr Lys Ser Phe Asn Arg
             210                 215                 220
Gly Glu Cys
225

<210> SEQ ID NO 4
<211> LENGTH: 214
<212> TYPE: PRT
<213> ORGANISM: Artificial
<220> FEATURE:
<223> OTHER INFORMATION: light chain 2 of 1+1 PD1TIM3_0389

<400> SEQUENCE: 4

Asn Ile Val Met Thr Pro Thr Pro Lys Phe Leu Pro Val Ser Ser Gly
 1               5                  10                  15
Asp Arg Val Thr Met Thr Cys Arg Ala Ser Gln Ser Val Asp Asn Tyr
                 20                  25                  30
Val Ala Trp Tyr Gln Gln Lys Pro Gly Gln Ser Pro Lys Leu Leu Ile
             35                  40                  45
Tyr Tyr Ala Ser Asn Arg Tyr Ile Gly Val Pro Asp Arg Phe Thr Gly
 50                  55                  60
Ser Gly Ser Gly Thr Asp Phe Thr Phe Thr Ile Ser Ser Val Gln Val
 65                  70                  75                  80
Glu Asp Leu Ala Val Tyr Phe Cys Gln Gln His Tyr Ser Ser Pro Tyr
                 85                  90                  95
Thr Phe Gly Ser Gly Thr Lys Leu Glu Ile Lys Arg Thr Val Ala Ala
             100                 105                 110
Pro Ser Val Phe Ile Phe Pro Pro Ser Asp Arg Lys Leu Lys Ser Gly
             115                 120                 125
Thr Ala Ser Val Val Cys Leu Leu Asn Asn Phe Tyr Pro Arg Glu Ala
             130                 135                 140
Lys Val Gln Trp Lys Val Asp Asn Ala Leu Gln Ser Gly Asn Ser Gln
```

```
145                 150                 155                 160
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 5
<211> LENGTH: 443
<212> TYPE: PRT
<213> ORGANISM: Artificial
<220> FEATURE:
<223> OTHER INFORMATION: heavy chain 1 of 1+1 PD1TIM3_0168 (based on
      chimeric PD1-0103 / Tim3-0018)

<400> SEQUENCE: 5

Lys Ile Val Leu Thr Gln Ser Pro Ala Ser Leu Pro Val Ser Leu Gly
1               5                   10                  15

Gln Arg Ala Thr Ile Ser Cys Arg Ala Ser Glu Ser Val Asp Thr Ser
                20                  25                  30

Asp Asn Ser Phe Ile His Trp Tyr Gln Gln Arg Pro Gly Gln Ser Pro
            35                  40                  45

Lys Leu Leu Ile Tyr Arg Ser Ser Thr Leu Glu Ser Gly Val Pro Ala
        50                  55                  60

Arg Phe Ser Gly Ser Gly Ser Arg Thr Asp Phe Thr Leu Thr Ile Asp
65                  70                  75                  80

Pro Val Glu Ala Asp Asp Val Ala Thr Tyr Tyr Cys Gln Gln Asn Tyr
                85                  90                  95

Asp Val Pro Trp Thr Phe Gly Gly Thr Lys Leu Glu Ile Lys Ser
                100                 105                 110

Ser Ala Ser Thr Lys Gly Pro Ser Val Phe Pro Leu Ala Pro Ser Ser
                115                 120                 125

Lys Ser Thr Ser Gly Gly Thr Ala Ala Leu Gly Cys Leu Val Lys Asp
                130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
                180                 185                 190

Thr Tyr Ile Cys Asn Val Asn His Lys Pro Ser Asn Thr Lys Val Asp
                195                 200                 205

Lys Lys Val Glu Pro Lys Ser Cys Asp Lys Thr His Thr Cys Pro Pro
                210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
                260                 265                 270

Trp Tyr Val Asp Gly Val Glu Val His Asn Ala Lys Thr Lys Pro Arg
                275                 280                 285
```

```
Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Gly Ala Pro Ile Glu Lys Thr Ile Ser Lys Ala Lys
                325                 330                 335

Gly Gln Pro Arg Glu Pro Gln Val Tyr Thr Leu Pro Pro Cys Arg Asp
            340                 345                 350

Glu Leu Thr Lys Asn Gln Val Ser Leu Trp Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
            435                 440

<210> SEQ ID NO 6
<211> LENGTH: 450
<212> TYPE: PRT
<213> ORGANISM: Artificial
<220> FEATURE:
<223> OTHER INFORMATION: heavy chain 2 of 1+1 PD1TIM3_0168

<400> SEQUENCE: 6

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Ser Val Gly Trp Ile Arg Gln Pro Ser Gly Lys Gly Leu Glu
        35                  40                  45

Trp Leu Ala His Ile Trp Leu Asn Asp Asp Val Phe Phe Asn Pro Ala
    50                  55                  60

Leu Lys Arg Arg Leu Thr Ile Ser Lys Asp Thr Ser Asn Asn Gln Val
65                  70                  75                  80

Phe Leu Gln Ile Ala Ser Val Val Thr Ala Asp Thr Ala Thr Tyr Tyr
                85                  90                  95

Cys Val Arg Ala Asn Gly Tyr Leu Tyr Ala Leu Asp Tyr Trp Gly Gln
            100                 105                 110

Gly Ile Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Glu Lys Val Glu Pro Lys Ser Cys Asp
    210                 215                 220
Lys Thr His Thr Cys Pro Pro Cys Pro Ala Pro Glu Ala Ala Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Gly Ala Pro Ile Glu
                325                 330                 335
Lys Thr Ile Ser Lys Ala Lys Gly Gln Pro Arg Glu Pro Gln Val Cys
            340                 345                 350
Thr Leu Pro Pro Ser Arg Asp Glu Leu Thr Lys Asn Gln Val Ser Leu
        355                 360                 365
Ser Cys Ala Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Val Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn Arg Phe Thr Gln Lys Ser Leu Ser Leu Ser Pro
        435                 440                 445
Gly Lys
    450

<210> SEQ ID NO 7
<211> LENGTH: 227
<212> TYPE: PRT
<213> ORGANISM: Artificial
<220> FEATURE:
<223> OTHER INFORMATION: light chain 1 of 1+1 PD1TIM3_0168

<400> SEQUENCE: 7

Glu Val Ile Leu Val Glu Ser Gly Gly Gly Leu Val Lys Pro Gly Gly
1               5                   10                  15
Ser Leu Lys Leu Ser Cys Ala Ala Ser Gly Phe Ser Phe Ser Ser Tyr
            20                  25                  30
Thr Met Ser Trp Val Arg Gln Thr Pro Glu Lys Arg Leu Asp Trp Val
        35                  40                  45
Ala Thr Ile Ser Gly Gly Gly Arg Asp Ile Tyr Tyr Pro Asp Ser Val
    50                  55                  60
Lys Gly Arg Phe Thr Ile Ser Arg Asp Asn Ala Lys Asn Thr Leu Tyr
65                  70                  75                  80
Leu Glu Met Ser Ser Leu Met Ser Glu Asp Thr Ala Leu Tyr Tyr Cys
                85                  90                  95
Val Leu Leu Thr Gly Arg Val Tyr Phe Ala Leu Asp Ser Trp Gly Gln
            100                 105                 110
```

```
Gly Thr Ser Val Thr Val Ser Ala Ser Val Ala Ala Pro Ser Val
            115                 120                 125

Phe Ile Phe Pro Pro Ser Asp Glu Gln Leu Lys Ser Gly Thr Ala Ser
130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 8
<211> LENGTH: 213
<212> TYPE: PRT
<213> ORGANISM: Artificial
<220> FEATURE:
<223> OTHER INFORMATION: light chain 2 of 1+1 PD1TIM3_0168

<400> SEQUENCE: 8

Gln Ile Val Leu Thr Gln Ser Pro Ala Ile Met Ser Ala Ser Pro Gly
1               5                   10                  15

Gln Lys Val Thr Ile Thr Cys Ser Ala Ser Ser Ser Val Asn Tyr Thr
            20                  25                  30

Gln Trp Tyr Gln Gln Lys Leu Gly Ser Ser Pro Lys Leu Trp Ile Tyr
        35                  40                  45

Asp Ala Phe Lys Leu Ala Pro Gly Val Pro Ala Arg Phe Ser Gly Ser
    50                  55                  60

Gly Thr Gly Thr Ser Tyr Ser Leu Thr Ile Ser Ser Met Glu Ala Glu
65                  70                  75                  80

Asp Ala Ala Ser Tyr Phe Cys His Gln Trp Ser Ser Tyr Pro Trp Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Arg Lys Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 9
<211> LENGTH: 443
```

<212> TYPE: PRT
<213> ORGANISM: Artificial
<220> FEATURE:
<223> OTHER INFORMATION: heavy chain 1 of 1+1 PD1TIM3_0476: (based on
      humanized PD1-0103_0312)/ Tim3-0438)

<400> SEQUENCE: 9

Asp Ile Val Met Thr Gln Ser Pro Asp Ser Leu Ala Val Ser Leu Gly
1               5                   10                  15

Glu Arg Ala Thr Ile Asn Cys Lys Ala Ser Glu Ser Val Asp Thr Ser
            20                  25                  30

Asp Asn Ser Phe Ile His Trp Tyr Gln Gln Lys Pro Gly Gln Ser Pro
        35                  40                  45

Lys Leu Leu Ile Tyr Arg Ser Ser Thr Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Asp Val Pro Trp Thr Phe Gly Gln Gly Thr Lys Val Glu Ile Lys Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Gly Ala Pro Ile Glu Lys Thr Ile Ser Lys Ala Lys
                325                 330                 335

Gly Gln Pro Arg Glu Pro Gln Val Tyr Thr Leu Pro Pro Cys Arg Asp
            340                 345                 350

Glu Leu Thr Lys Asn Gln Val Ser Leu Trp Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
        420                 425                 430

Thr Gln Lys Ser Leu Ser Leu Ser Pro Gly Lys
    435                 440

<210> SEQ ID NO 10
<211> LENGTH: 449
<212> TYPE: PRT
<213> ORGANISM: Artificial
<220> FEATURE:
<223> OTHER INFORMATION: heavy chain 2 of 1+1 PD1TIM3_0476

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Thr Thr
            20                  25                  30

Tyr Met His Trp Val Arg Gln Ala Pro Gly Lys Gly Leu Glu Trp Val
        35                  40                  45

Gly Arg Ile Asp Pro Ala Asp Asp Asn Thr Lys Tyr Ala Pro Lys Phe
    50                  55                  60

Gln Gly Lys Ala Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Val Arg Asp Phe Gly Tyr Val Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

```
Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 11
<211> LENGTH: 227
<212> TYPE: PRT
<213> ORGANISM: Artificial
<220> FEATURE:
<223> OTHER INFORMATION: light chain 1 of 1+1 PD1TIM3_0476

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Leu Leu Thr Gly Arg Val Tyr Phe Ala Leu Asp Ser Trp Gly Gln
            100                 105                 110

Gly Thr Leu Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205
```

```
Val Thr His Gln Gly Leu Ser Ser Pro Val Thr Lys Ser Phe Asn Arg
        210                 215                 220

Gly Glu Cys
225

<210> SEQ ID NO 12
<211> LENGTH: 214
<212> TYPE: PRT
<213> ORGANISM: Artificial
<220> FEATURE:
<223> OTHER INFORMATION: light chain 2 of 1+1 PD1TIM3_0476

<400> SEQUENCE: 12

Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Ser Val Asp Asn Tyr
            20                  25                  30

Val Ala Trp Tyr Leu Gln Lys Pro Gly Gln Ser Pro Gln Leu Leu Ile
        35                  40                  45

Tyr Tyr Ala Ser Asn Arg Tyr Ile Gly Val Pro Asp Arg Phe Ser Gly
50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln His Tyr Ser Ser Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 443
<212> TYPE: PRT
<213> ORGANISM: Artificial
<220> FEATURE:
<223> OTHER INFORMATION: heavy chain 1 of 1+1 PD1TIM3_0477: (based on
      humanized PD1-0103_0312) / Tim3-0434)

<400> SEQUENCE: 13

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Thr Ser
            20                  25                  30

Asp Asn Ser Phe Ile His Trp Tyr Gln Gln Lys Pro Gly Gln Ser Pro
        35                  40                  45

Lys Leu Leu Ile Tyr Arg Ser Ser Thr Leu Glu Ser Gly Val Pro Asp
```

```
            50                  55                  60
Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Tyr
                 85                  90                  95

Asp Val Pro Trp Thr Phe Gly Gln Gly Thr Lys Val Glu Ile Lys Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Gly Ala Pro Ile Glu Lys Thr Ile Ser Lys Ala Lys
                325                 330                 335

Gly Gln Pro Arg Glu Pro Gln Val Tyr Thr Leu Pro Pro Cys Arg Asp
            340                 345                 350

Glu Leu Thr Lys Asn Gln Val Ser Leu Trp Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 14
<211> LENGTH: 450
<212> TYPE: PRT
<213> ORGANISM: Artificial
```

<220> FEATURE:
<223> OTHER INFORMATION: heavy chain 2 of 1+1 PD1TIM3_0477

<400> SEQUENCE: 14

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Gly Leu Glu
        35                  40                  45

Trp Leu Ala His Ile Trp Leu Asn Asp Asp Val Phe Phe Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Thr Ala Thr Tyr Tyr
                85                  90                  95

Cys Val Arg Ala Asn Gly Tyr Leu Tyr Ala Leu Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Glu Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Val Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 15
<211> LENGTH: 227
<212> TYPE: PRT
<213> ORGANISM: Artificial
<220> FEATURE:
<223> OTHER INFORMATION: light chain 1 of 1+1 PD1TIM3_0477

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Thr Met Ser Trp Val Arg Gln Ala Pro Gly Lys Gly Leu Glu Trp Val
            35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Leu Leu Thr Gly Arg Val Tyr Phe Ala Leu Asp Ser Trp Gly Gln
            100                 105                 110

Gly Thr Leu Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 16
<211> LENGTH: 213
<212> TYPE: PRT
<213> ORGANISM: Artificial
<220> FEATURE:
<223> OTHER INFORMATION: light chain 2 of 1+1 PD1TIM3_0477

<400> SEQUENCE: 16

Asp Ile Gln Leu Thr Gln Ser Pro Ser Phe Leu Ser Ala Ser Val Gly
```

```
1               5                   10                  15
Asp Arg Val Thr Ile Thr Cys Ser Ala Ser Ser Ser Val Ser Tyr Thr
                20                  25                  30

Gln Trp Tyr Gln Gln Lys Pro Gly Lys Ala Pro Lys Leu Trp Ile Tyr
                35                  40                  45

Asp Ala Phe Lys Leu Ala Pro Gly Val Pro Ser Arg Phe Ser Gly Ser
            50                  55                  60

Gly Ser Gly Thr Glu Phe Thr Leu Thr Ile Ser Ser Leu Gln Pro Glu
65                  70                  75                  80

Asp Phe Ala Thr Tyr Phe Cys His Gln Trp Ser Ser Tyr Pro Trp Thr
                85                  90                  95

Phe Gly Gln Gly Thr Lys Leu Glu Ile Lys Arg Thr Val Ala Ala Pro
                100                 105                 110

Ser Val Phe Ile Phe Pro Pro Ser Asp Arg Lys Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
            210

<210> SEQ ID NO 17
<211> LENGTH: 443
<212> TYPE: PRT
<213> ORGANISM: Artificial
<220> FEATURE:
<223> OTHER INFORMATION: heavy chain 1 of 1+1 PD1TIM3_0166: (based on
      chimeric PD1-0103 / Tim3-0038)

<400> SEQUENCE: 17

Lys Ile Val Leu Thr Gln Ser Pro Ala Ser Leu Pro Val Ser Leu Gly
1               5                   10                  15

Gln Arg Ala Thr Ile Ser Cys Arg Ala Ser Glu Ser Val Asp Thr Ser
                20                  25                  30

Asp Asn Ser Phe Ile His Trp Tyr Gln Gln Arg Pro Gly Gln Ser Pro
                35                  40                  45

Lys Leu Leu Ile Tyr Arg Ser Ser Thr Leu Glu Ser Gly Val Pro Ala
            50                  55                  60

Arg Phe Ser Gly Ser Gly Ser Arg Thr Asp Phe Thr Leu Thr Ile Asp
65                  70                  75                  80

Pro Val Glu Ala Asp Asp Val Ala Thr Tyr Tyr Cys Gln Gln Asn Tyr
                85                  90                  95

Asp Val Pro Trp Thr Phe Gly Gly Gly Thr Lys Leu Glu Ile Lys Ser
                100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
130                 135                 140
```

-continued

```
Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Gln
        180                 185                 190

Thr Tyr Ile Cys Asn Val Asn His Lys Pro Ser Asn Thr Lys Val Asp
    195                 200                 205

Lys Lys Val Glu Pro Lys Ser Cys Asp Lys Thr His Thr Cys Pro Pro
210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Lys Phe Asn
        260                 265                 270

Trp Tyr Val Asp Gly Val Glu Val His Asn Ala Lys Thr Lys Pro Arg
    275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Gly Ala Pro Ile Glu Lys Thr Ile Ser Lys Ala Lys
            325                 330                 335

Gly Gln Pro Arg Glu Pro Gln Val Tyr Thr Leu Pro Pro Cys Arg Asp
        340                 345                 350

Glu Leu Thr Lys Asn Gln Val Ser Leu Trp Cys Leu Val Lys Gly Phe
    355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
        420                 425                 430

Thr Gln Lys Ser Leu Ser Leu Ser Pro Gly Lys
    435                 440
```

<210> SEQ ID NO 18
<211> LENGTH: 449
<212> TYPE: PRT
<213> ORGANISM: Artificial
<220> FEATURE:
<223> OTHER INFORMATION: heavy chain 2 of 1+1 PD1TIM3_0166

<400> SEQUENCE: 18

```
Glu Val Gln Leu Gln Gln Ser Gly Ala Glu Pro Leu Lys Pro Gly Ala
1               5                   10                  15

Ser Val Lys Leu Thr Cys Thr Thr Ser Gly Phe Asn Ile Lys Asp Tyr
            20                  25                  30

Tyr Ile His Trp Val Lys Gln Arg Ser Asp Gln Gly Leu Glu Trp Ile
        35                  40                  45

Gly Arg Ile Asp Pro Glu Asp Gly Glu Leu Ile Tyr Ala Pro Lys Phe
    50                  55                  60
```

Gln Asp Lys Ala Thr Ile Thr Val Asp Thr Ser Ser Asn Ile Ala Tyr
65                  70                  75                  80

Leu Gln Leu Asn Ser Leu Thr Ser Glu Asp Thr Ala Val Tyr Tyr Cys
                85                  90                  95

Ser Arg Asp His Gly Tyr Val Gly Trp Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Phe Thr Gln Lys Ser Leu Ser Leu Ser Pro Gly
        435                 440                 445

Lys

<210> SEQ ID NO 19
<211> LENGTH: 227
<212> TYPE: PRT
<213> ORGANISM: Artificial

<220> FEATURE:
<223> OTHER INFORMATION: light chain 1 of 1+1 PD1TIM3_0166

<400> SEQUENCE: 19

Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Ser Tyr
            20                  25                  30

Thr Met Ser Trp Val Arg Gln Thr Pro Glu Lys Arg Leu Asp Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Glu Met Ser Ser Leu Met Ser Glu Asp Thr Ala Leu Tyr Tyr Cys
                85                  90                  95

Val Leu Leu Thr Gly Arg Val Tyr Phe Ala Leu Asp Ser Trp Gly Gln
            100                 105                 110

Gly Thr Ser Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 20
<211> LENGTH: 214
<212> TYPE: PRT
<213> ORGANISM: Artificial
<220> FEATURE:
<223> OTHER INFORMATION: light chain 2 of 1+1 PD1TIM3_0166

<400> SEQUENCE: 20

Asn Val Val Met Thr Gln Ser Pro Lys Ser Met Ile Met Ser Val Gly
1               5                   10                  15

Gln Arg Val Thr Leu Asn Cys Lys Ala Ser Glu Asn Val Asp Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Arg Ser Ala Thr Asp Phe Thr Leu Thr Ile Ser Ser Val Gln Ala
65                  70                  75                  80

Glu Asp Leu Ala Val Tyr Tyr Cys Gly Gln Ser Tyr Ser Tyr Pro Trp
                85                  90                  95

Thr Phe Gly Gly Gly Thr Lys Leu Glu Phe Arg Arg Thr Val Ala Ala

```
                100             105             110
Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 21
<211> LENGTH: 685
<212> TYPE: PRT
<213> ORGANISM: Artificial
<220> FEATURE:
<223> OTHER INFORMATION: heavy chain of 2+2 PD1TIM3_0358: chimeric
      PD1-0103 / Tim3-0028

<400> SEQUENCE: 21

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Thr Thr
                20                  25                  30

Tyr Met His Trp Val Lys Gln Arg Pro Glu Gln Gly Leu Glu Trp Ile
            35                  40                  45

Gly Arg Ile Asp Pro Ala Asp Asp Asn Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Ala Ala Ile Tyr Tyr Cys
                85                  90                  95

Val Arg Asp Phe Gly Tyr Val Ala Trp Phe Ala Tyr Trp Gly Gln Gly
            100                 105                 110

Thr Leu Val Thr Phe Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Glu Lys Val Glu Pro Lys Ser Cys Asp Lys
            210                 215                 220

Thr His Thr Cys Pro Pro Cys Pro Ala Pro Glu Ala Ala Gly Gly Pro
225                 230                 235                 240
```

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Gly Gly Ser Gly Gly Gly Gly Ser Gly Gly Gly Gly Ser Gly
    450                 455                 460

Gly Gly Gly Ser Lys Ile Val Leu Thr Gln Ser Pro Ala Ser Leu Pro
465                 470                 475                 480

Val Ser Leu Gly Gln Arg Ala Thr Ile Ser Cys Arg Ala Ser Glu Ser
                485                 490                 495

Val Asp Thr Ser Asp Asn Ser Phe Ile His Trp Tyr Gln Gln Arg Pro
            500                 505                 510

Gly Gln Ser Pro Lys Leu Leu Ile Tyr Arg Ser Ser Thr Leu Glu Ser
        515                 520                 525

Gly Val Pro Ala Arg Phe Ser Gly Ser Gly Ser Arg Thr Asp Phe Thr
    530                 535                 540

Leu Thr Ile Asp Pro Val Glu Ala Asp Asp Val Ala Thr Tyr Tyr Cys
545                 550                 555                 560

Gln Gln Asn Tyr Asp Val Pro Trp Thr Phe Gly Gly Gly Thr Lys Leu
                565                 570                 575

Glu Ile Lys Ser Ser Ala Ser Thr Lys Gly Pro Ser Val Phe Pro Leu
            580                 585                 590

Ala Pro Ser Ser Lys Ser Thr Ser Gly Gly Thr Ala Ala Leu Gly Cys
        595                 600                 605

Leu Val Lys Asp Tyr Phe Pro Glu Pro Val Thr Val Ser Trp Asn Ser
    610                 615                 620

Gly Ala Leu Thr Ser Gly Val His Thr Phe Pro Ala Val Leu Gln Ser
625                 630                 635                 640

Ser Gly Leu Tyr Ser Leu Ser Ser Val Val Thr Val Pro Ser Ser Ser
                645                 650                 655

Leu Gly Thr Gln Thr Tyr Ile Cys Asn Val Asn His Lys Pro Ser Asn
```

```
                    660                 665                 670
Thr Lys Val Asp Lys Lys Val Glu Pro Lys Ser Cys Asp
            675                 680                 685

<210> SEQ ID NO 22
<211> LENGTH: 200
<212> TYPE: PRT
<213> ORGANISM: Artificial
<220> FEATURE:
<223> OTHER INFORMATION: light chain 1 of 2+2 PD1TIM3_0358

<400> SEQUENCE: 22

Asn Ile Val Met Thr Pro Thr Pro Lys Phe Leu Pro Val Ser Ser Gly
1               5                   10                  15

Asp Arg Val Thr Met Thr Cys Arg Ala Ser Gln Ser Val Asp Asn Tyr
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Ile Gly Val Pro Asp Arg Phe Thr Gly
    50                  55                  60

Ser Gly Ser Gly Thr Asp Phe Thr Phe Thr Ile Ser Ser Val Gln Val
65                  70                  75                  80

Glu Asp Leu Ala Val Tyr Phe Cys Gln Gln His Tyr Ser Ser Pro Tyr
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly
        195                 200

<210> SEQ ID NO 23
<211> LENGTH: 227
<212> TYPE: PRT
<213> ORGANISM: Artificial
<220> FEATURE:
<223> OTHER INFORMATION: light chain 2 of 2+2 PD1TIM3_0358

<400> SEQUENCE: 23

Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Ser Tyr
            20                  25                  30

Thr Met Ser Trp Val Arg Gln Thr Pro Glu Lys Arg Leu Asp Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80
```

```
Leu Glu Met Ser Ser Leu Met Ser Glu Asp Thr Ala Leu Tyr Tyr Cys
                85                  90                  95

Val Leu Leu Thr Gly Arg Val Tyr Phe Ala Leu Asp Ser Trp Gly Gln
            100                 105                 110

Gly Thr Ser Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 24
<211> LENGTH: 686
<212> TYPE: PRT
<213> ORGANISM: Artificial
<220> FEATURE:
<223> OTHER INFORMATION: heavy chain of 2+2 PD1TIM3_0359: chimeric
      PD1-0103 / Tim3-0018

<400> SEQUENCE: 24

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Ser Val Gly Trp Ile Arg Gln Pro Ser Gly Lys Gly Leu Glu
        35                  40                  45

Trp Leu Ala His Ile Trp Leu Asn Asp Asp Val Phe Phe Asn Pro Ala
    50                  55                  60

Leu Lys Arg Arg Leu Thr Ile Ser Lys Asp Thr Ser Asn Asn Gln Val
65                  70                  75                  80

Phe Leu Gln Ile Ala Ser Val Val Thr Ala Asp Thr Ala Thr Tyr Tyr
                85                  90                  95

Cys Val Arg Ala Asn Gly Tyr Leu Tyr Ala Leu Asp Tyr Trp Gly Gln
            100                 105                 110

Gly Ile Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

-continued

```
Pro Ser Asn Thr Lys Val Asp Glu Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Gly Gly Gly Gly Ser Gly Gly Gly Gly Ser Gly Gly Gly Gly Ser
450                 455                 460

Gly Gly Gly Gly Ser Lys Ile Val Leu Thr Gln Ser Pro Ala Ser Leu
465                 470                 475                 480

Pro Val Ser Leu Gly Gln Arg Ala Thr Ile Ser Cys Arg Ala Ser Glu
                485                 490                 495

Ser Val Asp Thr Ser Asp Asn Ser Phe Ile His Trp Tyr Gln Gln Arg
                500                 505                 510

Pro Gly Gln Ser Pro Lys Leu Leu Ile Tyr Arg Ser Ser Thr Leu Glu
            515                 520                 525

Ser Gly Val Pro Ala Arg Phe Ser Gly Ser Gly Ser Arg Thr Asp Phe
530                 535                 540

Thr Leu Thr Ile Asp Pro Val Glu Ala Asp Asp Val Ala Thr Tyr Tyr
545                 550                 555                 560

Cys Gln Gln Asn Tyr Asp Val Pro Trp Thr Phe Gly Gly Gly Thr Lys
                565                 570                 575

Leu Glu Ile Lys Ser Ser Ala Ser Thr Lys Gly Pro Ser Val Phe Pro
                580                 585                 590

Leu Ala Pro Ser Ser Lys Ser Thr Ser Gly Gly Thr Ala Ala Leu Gly
            595                 600                 605

Cys Leu Val Lys Asp Tyr Phe Pro Glu Pro Val Thr Val Ser Trp Asn
610                 615                 620
```

Ser Gly Ala Leu Thr Ser Gly Val His Thr Phe Pro Ala Val Leu Gln
625                 630                 635                 640

Ser Ser Gly Leu Tyr Ser Leu Ser Ser Val Val Thr Val Pro Ser Ser
            645                 650                 655

Ser Leu Gly Thr Gln Thr Tyr Ile Cys Asn Val Asn His Lys Pro Ser
        660                 665                 670

Asn Thr Lys Val Asp Lys Lys Val Glu Pro Lys Ser Cys Asp
    675                 680                 685

<210> SEQ ID NO 25
<211> LENGTH: 213
<212> TYPE: PRT
<213> ORGANISM: Artificial
<220> FEATURE:
<223> OTHER INFORMATION: light chain 1 of 2+2 PD1TIM3_0359

<400> SEQUENCE: 25

Gln Ile Val Leu Thr Gln Ser Pro Ala Ile Met Ser Ala Ser Pro Gly
1               5                   10                  15

Gln Lys Val Thr Ile Thr Cys Ser Ala Ser Ser Ser Val Asn Tyr Thr
            20                  25                  30

Gln Trp Tyr Gln Gln Lys Leu Gly Ser Ser Pro Lys Leu Trp Ile Tyr
        35                  40                  45

Asp Ala Phe Lys Leu Ala Pro Gly Val Pro Ala Arg Phe Ser Gly Ser
    50                  55                  60

Gly Thr Gly Thr Ser Tyr Ser Leu Thr Ile Ser Ser Met Glu Ala Glu
65                  70                  75                  80

Asp Ala Ala Ser Tyr Phe Cys His Gln Trp Ser Tyr Pro Trp Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Arg Lys Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 26
<211> LENGTH: 227
<212> TYPE: PRT
<213> ORGANISM: Artificial
<220> FEATURE:
<223> OTHER INFORMATION: light chain 2 of 2+2 PD1TIM3_0359

<400> SEQUENCE: 26

Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Ser Tyr
            20                  25                  30

```
Thr Met Ser Trp Val Arg Gln Thr Pro Glu Lys Arg Leu Asp Trp Val
         35                  40                  45

Ala Thr Ile Ser Gly Gly Arg Asp Ile Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Glu Met Ser Ser Leu Met Ser Glu Asp Thr Ala Leu Tyr Tyr Cys
                 85                  90                  95

Val Leu Leu Thr Gly Arg Val Tyr Phe Ala Leu Asp Ser Trp Gly Gln
                100                 105                 110

Gly Thr Ser Val Thr Val Ser Ser Ala Ser Val Ala Ala Pro Ser Val
                115                 120                 125

Phe Ile Phe Pro Pro Ser Asp Glu Gln Leu Lys Ser Gly Thr Ala Ser
            130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 27
<211> LENGTH: 685
<212> TYPE: PRT
<213> ORGANISM: Artificial
<220> FEATURE:
<223> OTHER INFORMATION: heavy chain of 2+2 PD1TIM3_0321: chimeric
      PD1-0103 / Tim3-0038

<400> SEQUENCE: 27

Glu Val Gln Leu Gln Gln Ser Gly Ala Glu Pro Leu Lys Pro Gly Ala
1               5                   10                  15

Ser Val Lys Leu Thr Cys Thr Thr Ser Gly Phe Asn Ile Lys Asp Tyr
            20                  25                  30

Tyr Ile His Trp Val Lys Gln Arg Ser Asp Gln Gly Leu Glu Trp Ile
        35                  40                  45

Gly Arg Ile Asp Pro Glu Asp Gly Glu Leu Ile Tyr Ala Pro Lys Phe
    50                  55                  60

Gln Asp Lys Ala Thr Ile Thr Val Asp Thr Ser Ser Asn Ile Ala Tyr
65                  70                  75                  80

Leu Gln Leu Asn Ser Leu Thr Ser Glu Asp Thr Ala Val Tyr Tyr Cys
                85                  90                  95

Ser Arg Asp His Gly Tyr Val Gly Trp Phe Ala Tyr Trp Gly Gln Gly
                100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Glu Asp Tyr Phe Pro Glu Pro Val Thr Val Ser Trp
```

-continued

```
        145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Glu Lys Val Glu Pro Lys Ser Cys Asp Lys
                210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Asn Ser Thr Tyr Arg Val
                290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Gly Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Asp Glu Leu Thr Lys Asn Gln Val Ser Leu Thr
                355                 360                 365
Cys Leu Val Lys Gly Phe Tyr Pro Ser Asp Ile Ala Val Glu Trp Glu
                370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
                435                 440                 445
Gly Gly Gly Gly Ser Gly Gly Gly Gly Ser Gly Gly Gly Gly Ser Gly
450                 455                 460
Gly Gly Gly Ser Lys Ile Val Leu Thr Gln Ser Pro Ala Ser Leu Pro
465                 470                 475                 480
Val Ser Leu Gly Gln Arg Ala Thr Ile Ser Cys Arg Ala Ser Glu Ser
                485                 490                 495
Val Asp Thr Ser Asp Asn Ser Phe Ile His Trp Tyr Gln Gln Arg Pro
                500                 505                 510
Gly Gln Ser Pro Lys Leu Leu Ile Tyr Arg Ser Ser Thr Leu Glu Ser
                515                 520                 525
Gly Val Pro Ala Arg Phe Ser Gly Ser Gly Ser Arg Thr Asp Phe Thr
                530                 535                 540
Leu Thr Ile Asp Pro Val Glu Ala Asp Asp Val Ala Thr Tyr Tyr Cys
545                 550                 555                 560
Gln Gln Asn Tyr Asp Val Pro Trp Thr Phe Gly Gly Gly Thr Lys Leu
                565                 570                 575
```

Glu Ile Lys Ser Ser Ala Ser Thr Lys Gly Pro Ser Val Phe Pro Leu
            580                 585                 590

Ala Pro Ser Ser Lys Ser Thr Ser Gly Gly Thr Ala Ala Leu Gly Cys
        595                 600                 605

Leu Val Lys Asp Tyr Phe Pro Glu Pro Val Thr Val Ser Trp Asn Ser
    610                 615                 620

Gly Ala Leu Thr Ser Gly Val His Thr Phe Pro Ala Val Leu Gln Ser
625                 630                 635                 640

Ser Gly Leu Tyr Ser Leu Ser Ser Val Val Thr Val Pro Ser Ser Ser
            645                 650                 655

Leu Gly Thr Gln Thr Tyr Ile Cys Asn Val Asn His Lys Pro Ser Asn
            660                 665                 670

Thr Lys Val Asp Lys Lys Val Glu Pro Lys Ser Cys Asp
            675                 680                 685

<210> SEQ ID NO 28
<211> LENGTH: 214
<212> TYPE: PRT
<213> ORGANISM: Artificial
<220> FEATURE:
<223> OTHER INFORMATION: light chain 1 of 2+2 PD1TIM3_0321

<400> SEQUENCE: 28

Asn Val Val Met Thr Gln Ser Pro Lys Ser Met Ile Met Ser Val Gly
1               5                   10                  15

Gln Arg Val Thr Leu Asn Cys Lys Ala Ser Glu Asn Val Asp Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Arg Ser Ala Thr Asp Phe Thr Leu Thr Ile Ser Ser Val Gln Ala
65                  70                  75                  80

Glu Asp Leu Ala Val Tyr Tyr Cys Gly Gln Ser Tyr Ser Tyr Pro Trp
                85                  90                  95

Thr Phe Gly Gly Gly Thr Lys Leu Glu Phe Arg Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29
<211> LENGTH: 227
<212> TYPE: PRT
<213> ORGANISM: Artificial

<220> FEATURE:
<223> OTHER INFORMATION: light chain 2 of 2+2 PD1TIM3_0321

<400> SEQUENCE: 29

Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Ser Tyr
            20                  25                  30

Thr Met Ser Trp Val Arg Gln Thr Pro Glu Lys Arg Leu Asp Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Glu Met Ser Ser Leu Met Ser Glu Asp Thr Ala Leu Tyr Tyr Cys
                85                  90                  95

Val Leu Leu Thr Gly Arg Val Tyr Phe Ala Leu Asp Ser Trp Gly Gln
            100                 105                 110

Gly Thr Ser Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 30
<211> LENGTH: 288
<212> TYPE: PRT
<213> ORGANISM: Homo sapiens

<400> SEQUENCE: 30

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

```
Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

```
<210> SEQ ID NO 31
<211> LENGTH: 5
<212> TYPE: PRT
<213> ORGANISM: Artificial Sequence
<220> FEATURE:
<223> OTHER INFORMATION: linker

<400> SEQUENCE: 31

Gly Gly Gly Gly Ser
1               5

<210> SEQ ID NO 32
<211> LENGTH: 192
<212> TYPE: PRT
<213> ORGANISM: Artificial Sequence
<220> FEATURE:
<223> OTHER INFORMATION: SNAP-tag

<400> SEQUENCE: 32

Asp Lys Asp Cys Glu Met Lys Arg Thr Thr Leu Asp Ser Pro Leu Gly
1               5                   10                  15

Lys Leu Glu Leu Ser Gly Cys Glu Gln Gly Leu His Glu Ile Lys Leu
            20                  25                  30

Leu Gly Lys Gly Thr Ser Ala Ala Asp Ala Val Glu Val Pro Ala Pro
        35                  40                  45

Ala Ala Val Leu Gly Gly Pro Glu Pro Leu Met Gln Ala Thr Ala Trp
    50                  55                  60

Leu Asn Ala Tyr Phe His Gln Pro Glu Ala Ile Glu Glu Phe Pro Val
65                  70                  75                  80

Pro Ala Leu His His Pro Val Phe Gln Gln Glu Ser Phe Thr Arg Gln
                85                  90                  95

Val Leu Trp Lys Leu Leu Lys Val Val Lys Phe Gly Glu Val Ile Ser
            100                 105                 110

Tyr Gln Gln Leu Ala Ala Leu Ala Gly Asn Pro Ala Ala Thr Ala Ala
        115                 120                 125
```

```
Val Lys Thr Ala Leu Ser Gly Asn Pro Val Pro Ile Leu Ile Pro Cys
    130                 135                 140

His Arg Val Val Ser Ser Gly Ala Val Gly Tyr Glu Gly Gly
145                 150                 155                 160

Leu Ala Val Lys Glu Trp Leu Leu Ala His Glu Gly His Arg Leu Gly
                165                 170                 175

Lys Pro Gly Leu Gly Pro Ala Gly Gly Ser Pro Gly Leu Glu Val Asn
            180                 185                 190
```

<210> SEQ ID NO 33
<211> LENGTH: 8
<212> TYPE: PRT
<213> ORGANISM: Artificial Sequence
<220> FEATURE:
<223> OTHER INFORMATION: Flag-tag

<400> SEQUENCE: 33

```
Asp Tyr Lys Asp Asp Asp Asp Lys
1               5
```

<210> SEQ ID NO 34
<211> LENGTH: 300
<212> TYPE: PRT
<213> ORGANISM: Homo sapiens

<400> SEQUENCE: 34

```
Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240
```

-continued

```
Ser Leu Ala Asn Leu Pro Pro Ser Gly Leu Ala Asn Ala Val Ala Glu
            245             250             255

Gly Ile Arg Ser Glu Glu Asn Ile Tyr Thr Ile Glu Glu Asn Val Tyr
        260             265             270

Glu Val Glu Glu Pro Asn Glu Tyr Tyr Cys Tyr Val Ser Ser Arg Gln
    275             280             285

Gln Pro Ser Gln Pro Leu Gly Cys Arg Phe Ala Met
290             295             300

<210> SEQ ID NO 35
<211> LENGTH: 181
<212> TYPE: PRT
<213> ORGANISM: Artificial Sequence
<220> FEATURE:
<223> OTHER INFORMATION: CLIP-tag

<400> SEQUENCE: 35

Asp Lys Asp Cys Glu Met Lys Arg Thr Thr Leu Asp Ser Pro Leu Gly
1               5                   10                  15

Lys Leu Glu Leu Ser Gly Cys Glu Gln Gly Leu His Arg Ile Ile Phe
            20                  25                  30

Leu Gly Lys Gly Thr Ser Ala Ala Asp Ala Val Glu Val Pro Ala Pro
        35                  40                  45

Ala Ala Val Leu Gly Gly Pro Glu Pro Leu Ile Gln Ala Thr Ala Trp
    50                  55                  60

Leu Asn Ala Tyr Phe His Gln Pro Glu Ala Ile Glu Glu Phe Pro Val
65                  70                  75                  80

Pro Ala Leu His His Pro Val Phe Gln Gln Glu Ser Phe Thr Arg Gln
                85                  90                  95

Val Leu Trp Lys Leu Leu Lys Val Val Lys Phe Gly Glu Val Ile Ser
            100                 105                 110

Glu Ser His Leu Ala Ala Leu Val Gly Asn Pro Ala Ala Thr Ala Ala
        115                 120                 125

Val Asn Thr Ala Leu Asp Gly Asn Pro Val Pro Ile Leu Ile Pro Cys
    130                 135                 140

His Arg Val Val Gln Gly Asp Ser Asp Val Gly Pro Tyr Leu Gly Gly
145                 150                 155                 160

Leu Ala Val Lys Glu Trp Leu Leu Ala His Glu Gly His Arg Leu Gly
                165                 170                 175

Lys Pro Gly Leu Gly
            180
```

CELLULAR BASED FRET ASSAY FOR THE DETERMINATION OF SIMULTANEOUS BINDING

CROSS-REFERENCE TO RELATED APPLICATIONS

This application is a continuation of, and claims priority to, International Patent Application No. PCT/EP2016/073186, filed on Sep. 29, 2016. This application also claims priority to European Patent Application No. 15188065.5, filed on Oct. 2, 2015. The entire contents of each of the above patent applications are hereby incorporated by reference.

SEQUENCE LISTING

The instant application contains a Sequence Listing which has been submitted electronically in ASCII format and is hereby incorporated by reference in its entirety. Said ASCII copy, created on Mar. 27, 2018, is named P33112US_SeqListing.txt and is 98,437 bytes in size.

BACKGROUND OF THE INVENTION

Herein is reported a cellular FRET assay for the determination of the simultaneous binding of a bispecific antibody to both of its targets/antigens.

The determination of functional binding of antibodies is a routine test made in drug development.

Fluorescence Resonance Energy Transfer (FRET) is a physical phenomenon first described over 50 years ago. FRET is based on the radiationless transfer of energy from a donor molecule to an acceptor molecule. No direct contact of both molecules is required therefore, i.e. it is a distance-dependent energy transfer. Thus, FRET can be used to investigate molecular interactions.

In US 2015/024410 is directed to an in vitro method for determining the binding of an antibody to an Fc receptor expressed in cell membranes or intact cells present in a measurement medium, comprising the following steps: (i) direct or indirect labeling of said Fc receptor with the first member of a pair of FRET partners, or else introducing, into the medium, cell membranes or intact cells whose Fc receptors were labeled beforehand directly with the first member of a pair of FRET partners; (ii) adding said antibody, labeled directly or indirectly with the second member of said pair of FRET partners, to the measurement medium; (iii) measuring the FRET signal, the existence of a FRET signal being representative of the binding of the antibody to the Fc receptor.

A method of measuring the binding activities of an antibody to both an antigen or antigen epitope and an Fc receptor or a fragment thereof, comprising: a step of mixing the antibody with the antigen or antigen epitope labeled with one member of a set of donor and acceptor capable of fluorescent resonance energy transfer and the Fc receptor or fragment thereof labeled with the other member of said set of donor and acceptor; a step of irradiating the resultant mixture with light having a wavelength capable of exciting the donor; and a step of measuring the fluorescence level of said mixture is reported in US 2010/190266.

In US 2006/165685 bispecific anti-Erb-B antibodies and their use in tumor therapy are reported.

In US 2015/0204847 a high-throughput, high-precision method for detecting protein structural changes in living cells is reported. Large stokes shift dyes are reported in US 2015/0090936. In US 2015/0044690 FRET measurement device and FRET measurement method are reported.

SUMMARY OF THE INVENTION

Herein is reported a method for the determination of the simultaneous binding of a bispecific antibody to a first and a second antigen/target comprising the following steps:
  a) incubating a cell expressing cell-membrane bound FRET-donor-tagged first antigen/target and FRET-acceptor-tagged second antigen/target with the bispecific antibody, and
  b) determining the simultaneous binding of the bispecific antibody by determining the energy transfer from the FRET-donor to the FRET-acceptor.

In one embodiment the cell-membrane bound FRET-donor and the cell-membrane bound FRET-acceptor comprise in N- to C-terminal direction:
  $H_2N$-antigen/target—FRET-donor/acceptor—transmembrane domain-COOH, or
  $H_2N$-FRET-donor/acceptor—antigen/target—transmembrane domain-COOH, or
  $H_2N$-FRET-donor/acceptor—transmembrane domain—antigen/target-COOH.

In one embodiment the FRET-donor and/or acceptor is a conjugate of a tag and a FRET-donor-fluorescent dye or a FRET-acceptor-fluorescent dye, respectively. In one embodiment the conjugate is a non-covalent conjugate and the FRET-donor-fluorescent dye and/or the FRET-acceptor-fluorescent dye is a fluorescent-dye conjugated antibody. In one embodiment the conjugate is a covalent conjugate, the tag is an enzyme and the FRET-donor-fluorescent dye and/or the FRET-acceptor-fluorescent dye are fluorescent dye labelled suicide enzyme substrates.

In one embodiment i) the FRET-donor or FRET-acceptor is a covalent complex of a SNAP-tag and a benzyl guanine, and ii) the FRET-acceptor or the FRET-donor is a covalent complex of a CLIP-tag and an O2-benzylcytosine, whereby the FRET-donor and the FRET-acceptor are different tags.

In one embodiment the bispecific antibody comprises one or two binding sites that specifically bind to the first antigen/target and one or two binding sites that specifically bind to the second antigen/target.

One aspect as reported herein is a method for determining for a bispecific antibody, which comprises a first binding site that specifically binds to a first antigen/target and a second binding site that specifically binds to a second antigen/target whereby the two binding sites bind with at least 10 fold difference in binding affinity to their respective antigens/targets, the binding interaction (strength) of the binding site that specifically binds to its antigen/target with the higher $K_D$-value comprising the following steps:
  a) incubating a cell expressing cell-membrane bound FRET-donor-tagged first antigen/target and FRET-acceptor-tagged second antigen/target with the bispecific antibody and determining the binding of the bispecific antibody by determining the energy transfer from the FRET-donor to the FRET-acceptor,
  b) repeating step a) in the presence of increasing concentrations of a monospecific antibody comprising the binding site of the bispecific antibody with the lower $K_D$ value, and c) determining the binding interaction (strength) by determining the concentration of the monospecific antibody at which the energy transfer from the FRET-donor to the FRET-acceptor is reduced.

In one embodiment the monospecific antibody is bivalent.

DETAILED DESCRIPTION OF THE INVENTION

The knobs into holes dimerization modules and their use in antibody engineering are described in Carter P.; Ridgway J. B. B.; Presta L. G.: Immunotechnology, Volume 2, Number 1, February 1996, pp. 73-73(1).

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, Md. (1991) is used for the light chain constant domain CL of kappa and lambda isotype, and the Kabat EU index numbering system (see pages 661-723) is used for the constant heavy chain domains (CH1, Hinge, CH2 and CH3, which is herein further clarified by referring to "numbering according to Kabat EU index" in this case).

I. Definitions

As used herein, the term "antigen" denotes the compound/moiety to which a binding site of an antibody binds. The antigen can be any moiety, i.e. target, to which an antibody can be generated, such as, e.g., a peptide, a polypeptide, a protein, a hapten, or a small molecule.

As used herein, the terms "FRET" and "fluorescence resonance energy transfer", denote a non-radiative energy transfer process that occurs between two chromophores.

The term "chromophore" denotes a moiety that includes a region that adsorbs certain wavelengths of light and interacts with such a region of another chromophore so as to be useful for FRET. Chromophores suitable for use in a FRET assay are known to the skilled person and are readily available. In one embodiment, a chromophore may be a donor (also referred to as a FRET-donor). A FRET-donor denotes a molecule that will absorb energy and then re-emit at least a portion of the energy over time. In one embodiment, a chromophore may be an acceptor (also referred to as a FRET-acceptor). A FRET-acceptor denotes a molecule that will accept energy radiationless from a FRET-donor, thus decreasing the donor's emission intensity and excited-state lifetime. Thus, provided that a FRET-donor and a FRET-acceptor are physically located sufficiently close (most often within 2.5 to 12 nm), the two FRET-moieties function together and, upon excitation with an appropriate wavelength, the FRET-donor transfers a precise amount of energy (proportional to the negative sixth power of the FRET-donor-FRET-acceptor distance) to the FRET-acceptor. This process can be specifically and quantitatively detected by observing the decrease in FRET-donor fluorescence intensity or lifetime or, in some cases, also the energy re-emitted by the FRET-acceptor as fluorescence.

A "multispecific antibody" denotes an antibody having binding specificities for at least two different epitopes on the same antigen or two different antigens. Multispecific antibodies can be prepared as full-length antibodies or antibody fragments (e.g. $F(ab')_2$ bispecific antibodies) or combinations thereof (e.g. full length antibody plus additional scFv or Fab fragments). Engineered antibodies with two, three or more (e.g. four) functional antigen binding sites have also been reported (see, e.g., US 2002/0004587 A1).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($k_d$). Affinity can be measured by common methods known in the art, such as surface plasmon resonance and including those described herein.

An "affinity matured" antibody refers to an antibody with one or more alterations in one or more hypervariable regions (HVRs), compared to a parent antibody which does not possess such alterations, such alterations resulting in an improvement in the affinity of the antibody for its antigen(s).

The term "antibody" herein is used in the broadest sense and encompasses various antibody structures, including but not limited to monoclonal antibodies, polyclonal antibodies, and multispecific antibodies (e.g., bispecific antibodies) so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called a, δ, ε, γ, and μ, respectively.

Cross-linking of receptors for the Fc-region of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al., Eur. J. Immunol. 29 (1999) 2613-2624), FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat), FcγRIII (CD16) binds IgG with medium to low affinity and exists as two types. FcγRIIIA is found on NK cells, macrophages, eosinophils and some monocytes and T cells and mediates ADCC. FcγRIIIB is highly expressed on neutrophils. Reduced binding to FcγRIIIA is found e.g. for antibodies comprising an IgG Fc-region with mutation at least at one of the amino acid residues E233-G236, P238, D265, N297, A327, P329, D270, Q295, A327, S239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al., J. Biol. Chem. 276 (2001) 6591-6604.

The terms "full length antibody", "intact antibody," and "whole antibody" are used herein interchangeably to refer to an antibody having a structure substantially similar to a native antibody structure or having heavy chains that contain an Fc-region as defined herein. A "full length antibody" is an antibody that comprises an antigen-binding variable region as well as a light chain constant domain (CL) and heavy chain constant domains, CH1, CH2 and CH3. The constant domains may be native sequence constant domains (e.g. human native sequence constant domains) or amino acid sequence variants thereof. In more detail a full length antibody comprises two antibody light chains (each comprising a light chain variable domain and a light chain constant domain) and two antibody heavy chains (each comprising a heavy chain variable domain, a hinge region and the heavy chain constant domains CH1, CH2 and CH3). The C-terminal amino acid residues K or GK may be present or not independently of each other in the two antibody heavy chains of a full length antibody.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

An "isolated" antibody is one, which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S., et al., J. Chromatogr. B 848 (2007) 79-87.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3), whereby between the first and the second constant domain a hinge region is located. Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

II. The Method as Reported Herein

Fluorescence Resonance Energy Transfer (FRET) is a physical phenomenon first described over 50 years ago. FRET is based on the radiationless transfer of energy from a donor molecule to an acceptor molecule. No direct contact of both molecules is required therefore, i.e. it is a distance-dependent energy transfer. Thus, FRET can be used to investigate molecular interactions.

The FRET-donor is the chromophore that initially absorbs the provided energy. The FRET-acceptor is the chromophore to which the energy is subsequently transferred from the FRET-donor. This interaction occurs without the conversion of the absorbed energy to thermal energy, and without requiring direct molecular interaction (e.g. by collision). The transfer of energy from the FRET-donor to the FRET-acceptor results in an increase in the FRET-acceptor's energy state. Finally, this results in the FRET-acceptor emitting radiation.

In order to FRET to occur beside the special proximity of the FRET-donor and the FRET-acceptor the excitation wavelength of the FRET-acceptor must be within the fluorescence emission spectrum of the FRET-donor.

The FRET-based energy transfer can in general be detected either by the appearance of the FRET-acceptor fluorescence or by the diminishing of the FRET-donor fluorescence. The FRET-donor is always a fluorescent molecule.

For the detection of FRET a number of different ways exist. As FRET effects that the fluorescence of the FRET-donor as well as that of the FRET-acceptor changes, a ratio of the two signals can be made, which is independent of the absolute concentration.

Fluorescence based spectroscopy provides exceptional sensitivity for biological assays, as the fluorescence to be determined is different in wavelength from excitation and background fluorescence. One drawback of fluorescence based spectroscopy methods used in biological assays is the variability of the intensity of the detectable signal (Gribbon et al., Drug Discov. Today 8 (2003) 1035; Gakamsky et al., Anal. Biochem. 409 (2011) 89; Thome et al., Curr. Opin. Chem. Biol. 14 (2010) 315).

Time-resolved fluorescence measurements have been established to improve assay performance as the time-resolved signal is largely independent of intensity variations (Moger et al., Screening 11 (2006) 765). The fluorescence lifetime is employed in methods such as moment analysis (Isenberg et al., Biophys. J. 9 (1969) 1337), multi-exponential fitting (Knutson et al., Chem. Phys. Lett. 102 (1983) 501; Beechem et al., Num. Comput. Methods 210 (1992) 37), or phasor analysis (Jameson et al., Methods 59 (2013) 278). It is used in biological fluorescence based assays such as resonance energy transfer (see e.g. in Lakowicz, Principles of Fluorescence Spectroscopy, 3rd ed. (Springer, New York, 2006)). Biological interactions have been measure using this approach (Jameson et al., Methods 59 (2013) 278; Dong et al., Biochem. Biophys. Res. Commun. 449 (2014) 196; Lebakken et al., J. Biomol. Screening 12 (2007) 828; Maltman et al., Chem. Commun. 46 (2010) 6929; Paterson et al., Anal. Biochem. 402 (2010) 54).

Methods employing fluorescence lifetime determinations include time-correlated single-photon counting (TCSPC), (Becker, The BH TCSPC Handbook, 5th ed. (Becker & Hickl, Berlin, 2012)), direct waveform recording (DWR) (Muretta et al., Rev. Sci. Instrum. 81 (2010) 103101).

The methods as reported herein are based on the change (increase or occurrence) of fluorescence resonance energy transfer (FRET) upon simultaneous binding of a multispecific antibody to two of its antigens. The antigens are presented as fusion proteins with a fluorophore on the outer cell membrane of a eukaryotic cell, whereby one antigen is fused with a FRET-donor fluorophore and the respective other antigen is fused with a FRET-acceptor fluorophore.

Herein is reported a method for the determination of the simultaneous binding of a multispecific antibody to a first and a second antigen comprising the following steps:
  a) incubating a cell expressing cell-membrane bound FRET-donor-tagged/FRET-donor-fused first antigen and FRET-acceptor-tagged/FRET-acceptor-fused second antigen with the multispecific antibody, and
  b) determining the simultaneous binding of the multispecific antibody by determining the energy transfer from the FRET-donor to the FRET-acceptor.

One aspect as reported herein is a method for determining for a bispecific antibody, which comprises a first binding site that specifically binds to a first antigen and a second binding site that specifically binds to a second antigen whereby the two binding sites bind with at least 10 fold difference in binding affinity to their respective antigens, the binding interaction (strength) of the binding site that specifically binds to its antigen with the higher $K_D$-value comprising the following steps:
  a) incubating a cell expressing cell-membrane bound FRET-donor-tagged/FRET-donor-fused first antigen and FRET-acceptor-tagged/FRET-acceptor-fused second antigen with the bispecific antibody and determining the binding of the bispecific antibody by determining the energy transfer from the FRET-donor to the FRET-acceptor,
  b) repeating step a) in the presence of increasing concentrations of a monospecific (bivalent) antibody comprising the binding site of the bispecific antibody with the lower $K_D$ value, and
  c) determining the binding interaction (strength) by determining the concentration of the monospecific (bivalent) antibody at which the energy transfer from the FRET-donor to the FRET-acceptor is reduced.

One aspect as reported herein is a method for determining simultaneous binding of a multispecific antibody to a first antigen and a second antigen by determining an alteration in fluorescence resonance energy transfer (FRET) between a first chromophore and a second chromophore comprising the following steps:
  providing a genetically engineered cell comprising the first antigen and the second antigen on the cell's outer surface/membrane, wherein the first antigen is fused to the first chromophore, and wherein the second antigen is fused to the second chromophore;
  contacting the cell with the multispecific antibody to form a mixture; and
  measuring the fluorescence lifetime of the first chromophore, the second chromophore, or the combination thereof,
  wherein a difference between the fluorescence lifetime in the presence of the multispecific antibody and the fluorescence lifetime in the absence of the multispecific antibody indicates that the multispecific antibody simultaneously binds to the first antigen and the second antigen.

In one embodiment the cell-membrane bound FRET-donor and the cell-membrane bound FRET-acceptor comprise in N- to C-terminal direction:

H$_2$N-antigen—FRET-donor/acceptor—transmembrane domain-COOH.

In one embodiment the FRET-donor and/or acceptor is a conjugate of a tag and a FRET-donor-fluorescent dye or a FRET-acceptor-fluorescent dye, respectively. In one embodiment the conjugate is a non-covalent conjugate and the FRET-donor-fluorescent dye and/or the FRET-acceptor-fluorescent dye is a fluorescent-dye conjugated antibody. In one embodiment the conjugate is a covalent conjugate, the tag is an enzyme and the FRET-donor-fluorescent dye and/or the FRET-acceptor-fluorescent dye are fluorescent dye labelled suicide enzyme substrates.

In one embodiment of all aspects and embodiments the FRET is a TR-FRET (time-resolved fluorescence resonance energy transfer).

In one embodiment of all aspects and embodiments the first chromophore is a FRET-donor and the second chromophore is a FRET-acceptor.

The FRET-donor and the FRET-acceptor are selected based on their suitability to perform FRET.

In one embodiment of all aspects and embodiments the chromophore is an amino acid to which a fluorescent dye is conjugated.

Examples of suitable chromophores include, but are not limited to, fluorescent proteins, including green fluorescent protein, red fluorescent protein, yellow fluorescent protein, and blue fluorescent protein. Green fluorescent protein and red fluorescent protein may be used as a FRET-donor-FRET-acceptor pair, and blue fluorescent protein and yellow fluorescent protein may be used as a FRET-donor-FRET-acceptor pair. The amino acid sequences of different version of green fluorescent protein, red fluorescent protein, yellow fluorescent protein, and blue fluorescent protein are known to the skilled person and are readily available, as are analogues of these proteins. Other chromophores include fluorescent dyes, such as fluorescent dyes that can be attached to a protein when the protein is present on a cell. Examples of such dyes are known in the art and are routinely used. Examples include dyes that react with cysteine, having with reactive iodoacetamide, maleimide, or thiosulfonate groups. Other examples include the protein labeling reagent FLASH-EDT2, a dye that can react with the domain CCXXCC (Invitrogen), and SNAP-tag, a self-labeling protein tag (New England Biolabs). Other fluorescent dyes are available that react specifically with an unnatural amino acid that is incorporated into a target protein by a modified tRNA.

Any appropriately selected two chromophores can be used as a FRET-donor-FRET-acceptor pair in the methods as reported herein, provided that the energy emitted by the FRET-donor (the emission spectrum) overlaps with the energy absorbed by the FRET-acceptor (the excitation spectrum), e.g., an energy transfer process (FRET) occurs between two chromophores. A FRET-donor and a FRET-acceptor that meet this overlap are referred to as a FRET-donor-FRET-acceptor pair. In one embodiment, FRET-donors that can be excited at longer wavelengths are superior to those excitable at shorter wavelengths. Also, probes with longer FLT (more than 3 nanoseconds (ns)) will be superior to probes with shorter FLT.

In one embodiment of all aspects and embodiments the FRET-donor is a fluorescent dye having an emission wavelength that overlaps with the excitation wavelength of the FRET-acceptor.

The FRET-donor as well as the FRET-acceptor can be inserted or fused to a polypeptide, i.e. the respective antigen, at the N-terminus, the C-terminus, or an internal site.

In one embodiment i) the FRET-donor or FRET-acceptor is a covalent complex of a SNAP-tag and a benzyl guanine, and ii) the FRET-acceptor or the FRET-donor is a covalent complex of a CLIP-tag and an O2-benzylcytosine, whereby the FRET-donor and the FRET-acceptor are different tags.

In one embodiment of all aspects and embodiments the FRET is initiated by mixing the cell and the multispecific antibody.

In one embodiment of all aspects and embodiments as reported herein the FRET-donor and the FRET-acceptor comprise a heterologous peptide domain to which a fluorescent dye can attach. In one embodiment the method as reported herein comprises the step of contacting the cell presenting the antigens on their surface with the appropriate protein labeling reagent for labeling the antigen with a fluorescent dye.

In one embodiment of all aspects and embodiments the FRET-donor and the FRET-acceptor are each a covalent conjugate of an enzyme and a fluorophore.

In one embodiment of all aspects and embodiments the difference between the fluorescence lifetime in the presence of the multispecific antibody and the fluorescence lifetime in the absence of the multispecific antibody is a decrease in the fluorescence lifetime of the FRET-donor.

In one embodiment of all aspects and embodiments the difference between the fluorescence lifetime in the presence of the multispecific antibody and the fluorescence lifetime in the absence of the multispecific antibody is an increase in the fluorescence lifetime of the FRET-acceptor.

In one embodiment of all aspects and embodiments the multispecific antibody is a bispecific antibody.

In one embodiment of all aspects and embodiments as reported herein the first antigen is different from the second antigen.

In one embodiment of all aspects as reported herein the first antigen and the second antigen are identical and the bispecific antibody binds to a first epitope on the first antigen and to a second epitope on the first antigen, whereby the first epitope does not overlap with the second epitope.

In one embodiment of all aspects and embodiments FRET is determined by determining the ratio of the emission signal of the FRET-donor to the emission signal of the FRET-acceptor or the ratio of the emission signal of the FRET-acceptor to the emission signal of the FRET-donor.

In one embodiment of all aspects and embodiments the emission wavelength bandwidth used for the determination is smaller than the excitation wavelength bandwidth.

In one embodiment of all aspects the cell is a eukaryotic cell. In one embodiment the cell is a HEK cell or a CHO cell.

In one embodiment in the method as reported herein FRET is determined at a single emission wavelength. In certain embodiments, the FRET fluorescence lifetime is determined at two or more wavelengths. In certain embodiments, the methods as reported herein are carried out in a well of a plate with a plurality of wells, such as a multi-well plate or a multi-domain multi-well plate.

III. Multispecific Antibodies

The antibodies of the current methods are multispecific antibodies.

In more detail, the antibody of the current methods is a multispecific antibody, e.g. a bispecific antibody. Multispecific antibodies are monoclonal antibodies that have binding specificities for at least two different targets. In certain embodiments, one of the binding specificities is for a first antigen/target and the other is for any other antigen/target. In certain embodiments, bispecific antibodies may bind to two different epitopes of the same antigen/target. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to [[PRO]] as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

The antibodies as in the current methods are at least bispecific antibodies. Bispecific antibodies are a member of the group of multispecific antibodies. Bispecific antibodies comprise at least two binding sites each formed by a pair of an antibody heavy chain variable domain (VH) and an antibody light chain variable domain (VL) binding to different antigens or to different epitopes on the same antigen. Such a bispecific antibody is an 1+1 format. Other bispecific antibody formats are 2+1 formats (comprising two binding sites for a first antigen or epitope and one binding site for a second antigen or epitope) or 2+2 formats (comprising two binding sites for a first antigen or epitope and two binding sites for a second antigen or epitope).

In one embodiment of all aspects the antibody of the current method comprises (all positions according to EU index of Kabat)

i) a homodimeric Fc-region of the human IgG1 subclass optionally with the mutations P329G, L234A and L235A, or ii) a homodimeric Fc-region of the human IgG4 subclass optionally with the mutations P329G, S228P and L235E, or iii) a homodimeric Fc-region of the human IgG1 subclass optionally with the mutations P329G, L234A, L235A, I253A, H310A, and H435A, or optionally with the mutations P329G, L234A, L235A, H310A, H433A, and Y436A, or iv) a heterodimeric Fc-region whereof
  a) one Fc-region polypeptide comprises the mutation T366W, and the other Fc-region polypeptide comprises the mutations T366S, L368A and Y407V, or
  b) one Fc-region polypeptide comprises the mutations T366W and Y349C, and the other Fc-region polypeptide comprises the mutations T366S, L368A, Y407V, and S354C, or
  c) one Fc-region polypeptide comprises the mutations T366W and S354C, and the other Fc-region polypeptide comprises the mutations T366S, L368A, Y407V and Y349C,
  or v) a heterodimeric Fc-region of the human IgG1 subclass whereof both Fc-region polypeptides comprise the mutations P329G, L234A and L235A and
  a) one Fc-region polypeptide comprises the mutation T366W, and the other Fc-region polypeptide comprises the mutations T366S, L368A and Y407V, or
  b) one Fc-region polypeptide comprises the mutations T366W and Y349C, and the other Fc-region polypeptide comprises the mutations T366S, L368A, Y407V, and S354C, or
  c) one Fc-region polypeptide comprises the mutations T366W and S354C, and the other Fc-region polypeptide comprises the mutations T366S, L368A, Y407V and Y349C,
  or vi) a heterodimeric Fc-region of the human IgG4 subclass whereof both Fc-region polypeptides comprise the mutations P329G, S228P and L235E and
  a) one Fc-region polypeptide comprises the mutation T366W, and the other Fc-region polypeptide comprises the mutations T366S, L368A and Y407V, or
  b) one Fc-region polypeptide comprises the mutations T366W and Y349C, and the other Fc-region polypeptide comprises the mutations T366S, L368A, Y407V, and S354C, or
  c) one Fc-region polypeptide comprises the mutations T366W and S354C, and the other Fc-region polypeptide comprises the mutations T366S, L368A, Y407V and Y349C,
  or vii) a combination of one of i), ii), and iii) with one of vi), v) and vi).

In one embodiment the multispecific antibody is a bivalent, bispecific antibody comprising
  a) a first light chain and a first heavy chain of an antibody specifically binding to a first antigen, and
  b) a second light chain and a second heavy chain of an antibody specifically binding to a second antigen, wherein the variable domains VL and VH of the second light chain and the second heavy chain are replaced by each other.

The antibody under a) does not contain a modification as reported under b) and the heavy chain and the light chain under a) are isolated chains.

In the antibody under b)
within the light chain
the variable light chain domain VL is replaced by the variable heavy chain domain VH of said antibody,
and
within the heavy chain
the variable heavy chain domain VH is replaced by the variable light chain domain VL of said antibody.

In one embodiment
i) in the constant domain CL of the first light chain under a) the amino acid at position 124 (numbering according to Kabat) is substituted by a positively charged amino acid, and wherein in the constant domain CH1 of the first heavy chain under a) the amino acid at position 147 or the amino acid at position 213 (numbering according to Kabat EU index) is substituted by a negatively charged amino acid,
or
ii) in the constant domain CL of the second light chain under b) the amino acid at position 124 (numbering according to Kabat) is substituted by a positively charged amino acid, and wherein in the constant domain CH1 of the second heavy chain under b) the amino acid at position 147 or the amino acid at position 213 (numbering according to Kabat EU index) is substituted by a negatively charged amino acid.

In one embodiment
i) in the constant domain CL of the first light chain under a) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the first heavy chain under a) the amino acid at position 147 or the amino acid at position 213 is substituted independently by glutamic acid (E) or aspartic acid (D) (numbering according to Kabat EU index),
or
ii) in the constant domain CL of the second light chain under b) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the second heavy chain under b) the amino acid at position 147 or the amino acid at position 213 is substituted independently by glutamic acid (E) or aspartic acid (D) (numbering according to Kabat EU index).

In one embodiment in the constant domain CL of the second heavy chain the amino acids at position 124 and 123 are substituted by K (numbering according to Kabat EU index).

In one embodiment in the constant domain CL of the second heavy chain the amino acid at position 123 is substituted by R and the amino acid as position 124 is substituted by K (numbering according to Kabat EU index).

In one embodiment in the constant domain CH1 of the second light chain the amino acids at position 147 and 213 are substituted by E (numbering according to EU index of Kabat).

In one embodiment in the constant domain CL of the first light chain the amino acids at position 124 and 123 are substituted by K, and in the constant domain CH1 of the first heavy chain the amino acids at position 147 and 213 are substituted by E (numbering according to Kabat EU index).

In one embodiment in the constant domain CL of the first light chain the amino acid at position 123 is substituted by R and the amino acid at position 124 is substituted by K, and in the constant domain CH1 of the first heavy chain the amino acids at position 147 and 213 are both substituted by E (numbering according to Kabat EU index).

In one embodiment in the constant domain CL of the second heavy chain the amino acids at position 124 and 123 are substituted by K, and wherein in the constant domain CH1 of the second light chain the amino acids at position 147 and 213 are substituted by E, and in the variable domain VL of the first light chain the amino acid at position 38 is substituted by K, in the variable domain VH of the first heavy chain the amino acid at position 39 is substituted by E, in the variable domain VL of the second heavy chain the amino acid at position 38 is substituted by K, and in the variable domain VH of the second light chain the amino acid at position 39 is substituted by E (numbering according to Kabat EU index).

In one embodiment the multispecific antibody is a bivalent, bispecific antibody comprising
a) a first light chain and a first heavy chain of an antibody specifically binding to a first antigen, and
b) a second light chain and a second heavy chain of an antibody specifically binding to a second antigen, wherein the variable domains VL and VH of the second light chain and the second heavy chain are replaced by each other, and wherein the constant domains CL and CH1 of the second light chain and the second heavy chain are replaced by each other.

The antibody under a) does not contain a modification as reported under b) and the heavy chain and the light chain and a) are isolated chains.

In the antibody under b)
within the light chain
the variable light chain domain VL is replaced by the variable heavy chain domain VH of said antibody, and the constant light chain domain CL is replaced by the constant heavy chain domain CH1 of said antibody;
and
within the heavy chain
the variable heavy chain domain VH is replaced by the variable light chain domain VL of said antibody, and the constant heavy chain domain CH1 is replaced by the constant light chain domain CL of said antibody.

In one embodiment the multispecific antibody is a bivalent, bispecific antibody comprising
a) a first light chain and a first heavy chain of an antibody specifically binding to a first antigen, and
b) a second light chain and a second heavy chain of an antibody specifically binding to a second antigen, wherein the constant domains CL and CH1 of the second light chain and the second heavy chain are replaced by each other.

The antibody under a) does not contain a modification as reported under b) and the heavy chain and the light chain under a) are isolated chains.

In the antibody under b)
within the light chain
the constant light chain domain CL is replaced by the constant heavy chain domain CH1 of said antibody;
and within the heavy chain
the constant heavy chain domain CH1 is replaced by the constant light chain domain CL of said antibody.

In one embodiment the multispecific antibody is a multispecific antibody comprising a) a full length antibody specifically binding to a first antigen and consisting of two antibody heavy chains and two antibody light chains, and
b) one, two, three or four single chain Fab fragments specifically binding to one to four further antigens (i.e. a second and/or third and/or fourth and/or fifth antigen, preferably specifically binding to one further antigen, i.e. a second antigen),
wherein said single chain Fab fragments under b) are fused to said full length antibody under a) via a peptidic linker at the C- or N-terminus of the heavy or light chain of said full length antibody.

In one embodiment one or two identical single chain Fab fragments binding to a second antigen are fused to the full length antibody via a peptidic linker at the C-terminus of the heavy or light chains of said full length antibody.

In one embodiment one or two identical single chain Fab fragments binding to a second antigen are fused to the full length antibody via a peptidic linker at the C-terminus of the heavy chains of said full length antibody.

In one embodiment one or two identical single chain Fab fragments binding to a second antigen are fused to the full length antibody via a peptidic linker at the C-terminus of the light chains of said full length antibody.

In one embodiment two identical single chain Fab fragments binding to a second antigen are fused to the full length antibody via a peptidic linker at the C-terminus of each heavy or light chain of said full length antibody.

In one embodiment two identical single chain Fab fragments binding to a second antigen are fused to the full length antibody via a peptidic linker at the C-terminus of each heavy chain of said full length antibody.

In one embodiment two identical single chain Fab fragments binding to a second antigen are fused to the full length antibody via a peptidic linker at the C-terminus of each light chain of said full length antibody.

In one embodiment the multispecific antibody is a trivalent, bispecific antibody comprising
a) a full length antibody specifically binding to a first antigen and consisting of two antibody heavy chains and two antibody light chains,
b) a first polypeptide consisting of
ba) an antibody heavy chain variable domain (VH), or
bb) an antibody heavy chain variable domain (VH) and an antibody constant domain 1 (CH1),
wherein said first polypeptide is fused with the N-terminus of its VH domain via a peptidic linker to the C-terminus of one of the two heavy chains of said full length antibody,
c) a second polypeptide consisting of
ca) an antibody light chain variable domain (VL), or
cb) an antibody light chain variable domain (VL) and an antibody light chain constant domain (CL),
wherein said second polypeptide is fused with the N-terminus of the VL domain via a peptidic linker to the C-terminus of the other of the two heavy chains of said full length antibody,
and
wherein the antibody heavy chain variable domain (VH) of the first polypeptide and the antibody light chain variable domain (VL) of the second polypeptide together form an antigen-binding site specifically binding to a second antigen.

In one embodiment the antibody heavy chain variable domain (VH) of the polypeptide under b) and the antibody light chain variable domain (VL) of the polypeptide under c) are linked and stabilized via an interchain disulfide bridge by introduction of a disulfide bond between the following positions:
i) heavy chain variable domain position 44 to light chain variable domain position 100, or
ii) heavy chain variable domain position 105 to light chain variable domain position 43, or
iii) heavy chain variable domain position 101 to light chain variable domain position 100 (numbering always according to Kabat EU index).

Techniques to introduce unnatural disulfide bridges for stabilization are described e.g. in WO 94/029350, Rajagopal, V., et al., Prot. Eng. (1997) 1453-1459; Kobayashi, H., et al., Nucl. Med. Biol. 25 (1998) 387-393; and Schmidt, M., et al., Oncogene 18 (1999) 1711-1721. In one embodiment the optional disulfide bond between the variable domains of the polypeptides under b) and c) is between heavy chain variable domain position 44 and light chain variable domain position 100. In one embodiment the optional disulfide bond between the variable domains of the polypeptides under b) and c) is between heavy chain variable domain position 105 and light chain variable domain position 43 (numbering always according to Kabat). In one embodiment a trivalent, bispecific antibody without said optional disulfide stabilization between the variable domains VH and VL of the single chain Fab fragments is preferred.

In one embodiment the multispecific antibody is a trispecific or tetraspecific antibody, comprising
a) a first light chain and a first heavy chain of a full length antibody which specifically binds to a first antigen, and
b) a second (modified) light chain and a second (modified) heavy chain of a full length antibody which specifically binds to a second antigen, wherein the variable domains VL and VH are replaced by each other, and/or wherein the constant domains CL and CH1 are replaced by each other, and
c) wherein one to four antigen binding peptides which specifically bind to one or two further antigens (i.e. to a third and/or fourth antigen) are fused via a peptidic linker to the C- or N-terminus of the light chains or heavy chains of a) and/or b).

The antibody under a) does not contain a modification as reported under b) and the heavy chain and the light chain and a) are isolated chains.

In one embodiment the trispecific or tetraspecific antibody comprises under c) one or two antigen binding peptides which specifically bind to one or two further antigens.

In one embodiment the antigen binding peptides are selected from the group of a scFv fragment and a scFab fragment.

In one embodiment the antigen binding peptides are scFv fragments.

In one embodiment the antigen binding peptides are scFab fragments.

In one embodiment the antigen binding peptides are fused to the C-terminus of the heavy chains of a) and/or b).

In one embodiment the trispecific or tetraspecific antibody comprises under c) one or two antigen binding peptides which specifically bind to one further antigen.

In one embodiment the trispecific or tetraspecific antibody comprises under c) two identical antigen binding peptides which specifically bind to a third antigen. In one preferred embodiment such two identical antigen binding peptides are fused both via the same peptide linker to the C-terminus of the heavy chains of a) and b). In one preferred embodiment the two identical antigen binding peptides are either a scFv fragment or a scFab fragment.

In one embodiment the trispecific or tetraspecific antibody comprises under c) two antigen binding peptides which specifically bind to a third and a fourth antigen. In one embodiment said two antigen binding peptides are fused both via the same peptide connector to the C-terminus of the heavy chains of a) and b). In one preferred embodiment said two antigen binding peptides are either a scFv fragment or a scFab fragment.

In one embodiment the multispecific antibody is a bispecific, tetravalent antibody comprising
- a) two light chains and two heavy chains of an antibody, which specifically bind to a first antigen (and comprise two Fab fragments),
- b) two additional Fab fragments of an antibody, which specifically bind to a second antigen, wherein said additional Fab fragments are fused both via a peptidic linker either to the C- or N-termini of the heavy chains of a), and
wherein in the Fab fragments the following modifications were performed
- i) in both Fab fragments of a), or in both Fab fragments of b), the variable domains VL and VH are replaced by each other, and/or the constant domains CL and CH1 are replaced by each other, or
- ii) in both Fab fragments of a) the variable domains VL and VH are replaced by each other, and the constant domains CL and CH1 are replaced by each other,
and
in both Fab fragments of b) the variable domains VL and VH are replaced by each other, or the constant domains CL and CH1 are replaced by each other, or
- iii) in both Fab fragments of a) the variable domains VL and VH are replaced by each other, or the constant domains CL and CH1 are replaced by each other,
and
in both Fab fragments of b) the variable domains VL and VH are replaced by each other, and the constant domains CL and CH1 are replaced by each other, or
- iv) in both Fab fragments of a) the variable domains VL and VH are replaced by each other, and in both Fab fragments of b) the constant domains CL and CH1 are replaced by each other, or
- v) in both Fab fragments of a) the constant domains CL and CH1 are replaced by each other, and in both Fab fragments of b) the variable domains VL and VH are replaced by each other.

In one embodiment said additional Fab fragments are fused both via a peptidic linker either to the C-termini of the heavy chains of a), or to the N-termini of the heavy chains of a).

In one embodiment said additional Fab fragments are fused both via a peptidic linker either to the C-termini of the heavy chains of a).

In one embodiment said additional Fab fragments are fused both via a peptide connector to the N-termini of the heavy chains of a).

In one embodiment in the Fab fragments the following modifications are performed:
- i) in both Fab fragments of a), or in both Fab fragments of b), the variable domains VL and VH are replaced by each other,
and/or
the constant domains CL and CH1 are replaced by each other.

In one embodiment in the Fab fragments the following modifications are performed:
- i) in both Fab fragments of a) the variable domains VL and VH are replaced by each other,
and/or
the constant domains CL and CH1 are replaced by each other.

In one embodiment in the Fab fragments the following modifications are performed:
- i) in both Fab fragments of a) the constant domains CL and CH1 are replaced by each other.

In one embodiment in the Fab fragments the following modifications are performed:
- i) in both Fab fragments of b) the variable domains VL and VH are replaced by each other,
and/or
the constant domains CL and CH1 are replaced by each other.

In one embodiment in the Fab fragments the following modifications are performed:
- i) in both Fab fragments of b) the constant domains CL and CH1 are replaced by each other.

In one embodiment the multispecific antibody is a bispecific, tetravalent antibody comprising:
- a) a (modified) heavy chain of a first antibody, which specifically binds to a first antigen and comprises a first VH-CH1 domain pair, wherein to the C-terminus of said heavy chain the N-terminus of a second VH-CH1 domain pair of said first antibody is fused via a peptidic linker,
- b) two light chains of said first antibody of a),
- c) a (modified) heavy chain of a second antibody, which specifically binds to a second antigen and comprises a first VH-CL domain pair, wherein to the C-terminus of said heavy chain the N-terminus of a second VH-CL domain pair of said second antibody is fused via a peptidic linker, and
- d) two (modified) light chains of said second antibody of c), each comprising a CL-CH1 domain pair.

In one embodiment the multispecific antibody is a bispecific antibody comprising
- a) the heavy chain and the light chain of a first full length antibody that specifically binds to a first antigen, and
- b) the heavy chain and the light chain of a second full length antibody that specifically binds to a second antigen, wherein the N-terminus of the heavy chain is connected to the C-terminus of the light chain via a peptidic linker.

The antibody under a) does not contain a modification as reported under b) and the heavy chain and the light chain are isolated chains.

In one embodiment the multispecific antibody is a bispecific antibody comprising
- a) a full length antibody specifically binding to a first antigen and consisting of two antibody heavy chains and two antibody light chains, and
- b) an Fv fragment specifically binding to a second antigen comprising a VH2 domain and a VL2 domain, wherein both domains are connected to each other via a disulfide bridge, wherein only either the VH2 domain or the VL2 domain is fused via a peptidic linker to the heavy or light chain of the full length antibody specifically binding to a first antigen.

In the bispecific the heavy chains and the light chains under a) are isolated chains.

In one embodiment the other of the VH2 domain or the VL2 domain is not fused via a peptide linker to the heavy or light chain of the full length antibody specifically binding to a first antigen.

In all aspects as reported herein the first light chain comprises a VL domain and a CL domain and the first heavy chain comprises a VH domain, a CH1 domain, a hinge region, a CH2 domain and a CH3 domain.

In one embodiment the multispecific antibody is a bispecific trivalent antibody comprising
- a) two Fab fragments that specifically binds to a first antigen,
- b) one CrossFab fragment that specifically binds to a second antigen in which the CH1 and the CL domain are exchanged for each other,
- c) one Fc-region comprising a first Fc-region heavy chain and a second Fc-region heavy chain,
wherein the C-terminus of CH1 domains of the two Fab fragments are connected to the N-terminus of the heavy chain Fc-region polypeptides, and wherein the C-terminus of the CL domain of the CrossFab fragment is connected to the N-terminus of the VH domain of one of the Fab fragments.

In one embodiment the multispecific antibody is a bispecific trivalent antibody comprising
- a) two Fab fragments that specifically binds to a first antigen,
- b) one CrossFab fragment that specifically binds to a second antigen in which the CH1 and the CL domain are exchanged for each other,
- c) one Fc-region comprising a first Fc-region heavy chain and a second Fc-region heavy chain,
wherein the C-terminus of CH1 domain of the first Fab fragment is connected to the N-terminus of one of the heavy chain Fc-region polypeptides and the C-terminus of the CL-domain of the CrossFab fragment is connected to the N-terminus of the other heavy chain Fc-region polypeptide, and wherein the C-terminus of the CH1 domain of the second Fab fragment is connected to the N-terminus of the VH domain of the first Fab fragment or to the N-terminus of the VH domain of the CrossFab fragment.

In one embodiment the multispecific antibody is a bispecific antibody comprising
- a) a full length antibody specifically binding to a first antigen and consisting of two antibody heavy chains and two antibody light chains, and
- b) a Fab fragment specifically binding to a second antigen comprising a VH2 domain and a VL2 domain comprising a heavy chain fragment and a light chain fragment, wherein
   within the light chain fragment
      the variable light chain domain VL2 is replaced by the variable heavy chain domain VH2 of said antibody,
      and
   within the heavy chain fragment
      the variable heavy chain domain VH2 is replaced by the variable light chain domain VL2 of said antibody
wherein the heavy chain Fab fragment is inserted between the CH1 domain of one of the heavy chains of the full length antibody and the respective Fc-region of the full length antibody, and the N-terminus of the light chain Fab fragment is conjugated to the C-terminus of the light chain of the full length antibody that is paired with the heavy chain of the full length antibody into which the heavy chain Fab fragment has been inserted.

In one embodiment the multispecific antibody is a bispecific antibody comprising
- a) a full length antibody specifically binding to a first antigen and consisting of two antibody heavy chains and two antibody light chains, and
- b) a Fab fragment specifically binding to a second antigen comprising a VH2 domain and a VL2 domain comprising a heavy chain fragment and a light chain fragment, wherein
   within the light chain fragment
      the variable light chain domain VL2 is replaced by the variable heavy chain domain VH2 of said antibody,
      and
   within the heavy chain fragment
      the variable heavy chain domain VH2 is replaced by the variable light chain domain VL2 of said antibody
wherein the C-terminus of the heavy chain fragment of the Fab fragment is conjugated to the N-terminus of one of the heavy chains of the full length antibody and the C-terminus of the light chain fragment of the Fab fragment is conjugated to the N-terminus of the light chain of the full length antibody that pairs with the heavy chain of the full length antibody to which the heavy chain fragment of the Fab fragment is conjugated.

In one embodiment of all aspects the antibody as reported herein is a multispecific antibody, which requires heterodimerization of at least two heavy chain polypeptides.

Several approaches for CH3-modifications in order to support heterodimerization have been described, for example in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291. Typically, in the approaches known in the art, the CH3 domain of the first heavy chain and the CH3 domain of the second heavy chain are both engineered in a complementary manner so that the heavy chain comprising one engineered CH3 domain can no longer homodimerize with another heavy chain of the same structure (e.g. a CH3-engineered first heavy chain can no longer homodimerize with another CH3-engineered first heavy chain; and a CH3-engineered second heavy chain can no longer homodimerize with another CH3-engineered second heavy chain). Thereby the heavy chain comprising one engineered CH3 domain is forced to heterodimerize with another heavy chain comprising the CH3 domain, which is engineered in a complementary manner. For this embodiment, the CH3 domain of the first heavy chain and the CH3 domain of the second heavy chain are engineered in a complementary manner by amino acid substitutions, such that the first heavy chain and the second heavy chain are forced to heterodimerize, whereas the first heavy chain and the second heavy chain can no longer homodimerize (e.g. for steric reasons).

The different approaches for supporting heavy chain heterodimerization known in the art, that were cited and included above, are contemplated as different alternatives used in providing a multispecific antibody as reported herein, which comprises a "non-crossed Fab region" derived from a first antibody, which specifically binds to a first antigen, and a "crossed Fab region" derived from a second antibody, which specifically binds to a second antigen, in combination with the particular amino acid substitutions described above.

The CH3 domains of the multispecific antibody as reported herein can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotechnol. 16 (1998) 677-681; Atwell, S., et al., J. Mol. Biol. 270 (1997) 26-35) and increases the yield.

In one preferred embodiment the multispecific antibody comprises a T366W mutation in the CH3 domain of the "knobs chain" and the mutations T366S, L368A, Y407V in the CH3 domain of the "hole-chain" (numbering according to Kabat EU index). An additional interchain disulfide bridge between the CH3 domains can also be used (Merchant, A. M., et al., Nature Biotechnol. 16 (1998) 677-681) e.g. by introducing a Y349C mutation into the CH3 domain of the "knobs chain" and a E356C mutation or a S354C mutation into the CH3 domain of the "hole chain". Thus, in a another preferred embodiment, the multispecific antibody comprises the mutations Y349C and T366W in one of the two CH3 domains and the mutations E356C, T366S, L368A and Y407V in the other of the two CH3 domains or the multispecific antibody comprises the mutations Y349C and T366W in one of the two CH3 domains and the mutations S354C, T366S, L368A and Y407V in the other of the two CH3 domains (the additional Y349C mutation in one CH3 domain and the additional E356C or S354C mutation in the other CH3 domain forming a interchain disulfide bridge) (numbering according to Kabat EU index).

But also other knobs-in-holes technologies as described by EP 1 870 459, can be used alternatively or additionally. In one embodiment the multispecific antibody comprises the mutations R409D and K370E in the CH3 domain of the "knobs chain" and the mutations D399K and E357K in the CH3 domain of the "hole-chain" (numbering according to Kabat EU index).

In one embodiment the multispecific antibody comprises a T366W mutation in the CH3 domain of the "knobs chain" and the mutations T366S, L368A and Y407V in the CH3 domain of the "hole chain" and additionally the mutations R409D and K370E in the CH3 domain of the "knobs chain" and the mutations D399K and E357K in the CH3 domain of the "hole chain" (numbering according to the Kabat EU index).

In one embodiment the multispecific antibody comprises the mutations Y349C and T366W in one of the two CH3 domains and the mutations S354C, T366S, L368A and Y407V in the other of the two CH3 domains, or the multispecific antibody comprises the mutations Y349C and T366W in one of the two CH3 domains and S354C, T366S, L368A and Y407V in the other of the two CH3 domains and additionally the mutations R409D and K370E in the CH3 domain of the "knobs chain" and the mutations D399K and E357K in the CH3 domain of the "hole chain" (numbering according to the Kabat EU index).

Apart from the "knob-into-hole technology" other techniques for modifying the CH3 domains of the heavy chains of a multispecific antibody to enforce heterodimerization are known in the art. These technologies, especially the ones described in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954 and WO 2013/096291 are contemplated herein as alternatives to the "knob-into-hole technology" in combination with a multispecific antibody.

In one embodiment in the multispecific antibody the approach described in EP 1870459 is used to support heterodimerization of the first heavy chain and the second heavy chain of the multispecific antibody. This approach is based on the introduction of charged amino acids with opposite charges at specific amino acid positions in the CH3/CH3-domain-interface between both, the first and the second heavy chain.

Accordingly, in this embodiment in the tertiary structure of the multispecific antibody the CH3 domain of the first heavy chain and the CH3 domain of the second heavy chain form an interface that is located between the respective antibody CH3 domains, wherein the respective amino acid sequences of the CH3 domain of the first heavy chain and the amino acid sequence of the CH3 domain of the second heavy chain each comprise a set of amino acids that is located within said interface in the tertiary structure of the antibody, wherein from the set of amino acids that is located in the interface in the CH3 domain of one heavy chain a first amino acid is substituted by a positively charged amino acid and from the set of amino acids that is located in the interface in the CH3 domain of the other heavy chain a second amino acid is substituted by a negatively charged amino acid. The multispecific antibody according to this embodiment is herein also referred to as "CH3(+/−)-engineered multispecific antibody" (wherein the abbreviation "+/−" stands for the oppositely charged amino acids that were introduced in the respective CH3 domains).

In one embodiment of the CH3(+/−)-engineered multispecific antibody the positively charged amino acid is selected from K, R and H, and the negatively charged amino acid is selected from E or D.

In one embodiment of the CH3(+/−)-engineered multispecific antibody the positively charged amino acid is selected from K and R, and the negatively charged amino acid is selected from E or D.

In one embodiment of the CH3(+/−)-engineered multispecific antibody the positively charged amino acid is K, and the negatively charged amino acid is E.

In one embodiment of the CH3(+/−)-engineered multispecific antibody in the CH3 domain of one heavy chain the amino acid R at position 409 is substituted by D and the amino acid K at position is substituted by E, and in the CH3 domain of the other heavy chain the amino acid D at position 399 is substituted by K and the amino acid E at position 357 is substituted by K (numbering according to Kabat EU index).

In one embodiment the approach described in WO 2013/157953 is used to support heterodimerization of the first heavy chain and the second heavy chain of the multispecific antibody. In one embodiment in the CH3 domain of one heavy chain the amino acid T at position 366 is substituted by K, and in the CH3 domain of the other heavy chain the amino acid L at position 351 is substituted by D (numbering according to Kabat EU index). In another embodiment in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index).

In another embodiment in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index). Additionally at least one of the following substitutions is comprised in the CH3 domain of the other heavy chain: the amino acid Y at position 349 is substituted by E, the amino acid Y at position 349 is substituted by D and the amino acid L at position 368 is substituted by E (numbering according to Kabat EU index). In one embodiment the amino acid L at position 368 is substituted by E (numbering according to Kabat EU index).

In one embodiment the approach described in WO 2012/058768 is used to support heterodimerization of the first heavy chain and the second heavy chain of the multispecific antibody. In one embodiment in the CH3 domain of one heavy chain the amino acid L at position 351 is substituted by Y and the amino acid Y at position 407 is substituted by A, and in the CH3 domain of the other heavy chain the amino acid T at position 366 is substituted by A and the amino acid K at position 409 is substituted by F (numbering according to Kabat EU index). In another embodiment, in addition to the aforementioned substitutions, in the CH3 domain of the other heavy chain at least one of the amino acids at positions 411 (originally T), 399 (originally D), 400 (originally S), 405 (originally F), 390 (originally N) and 392 (originally K) is substituted (numbering according to Kabat EU index). Preferred substitutions are:

substituting the amino acid T at position 411 by an amino acid selected from N, R, Q, K, D, E and W (numbering according to Kabat EU index),
substituting the amino acid D at position 399 by an amino acid selected from R, W, Y, and K (numbering according to Kabat EU index),
substituting the amino acid S at position 400 by an amino acid selected from E, D, R and K (numbering according to Kabat EU index),
substituting the amino acid F at position 405 by an amino acid selected from I, M, T, S, V and W (numbering according to Kabat EU index;
substituting the amino acid N at position 390 by an amino acid selected from R, K and D (numbering according to Kabat EU index; and
substituting the amino acid K at position 392 by an amino acid selected from V, M, R, L, F and E (numbering according to Kabat EU index).

In another embodiment of the multispecific antibody (engineered according to WO 2012/058768), in the CH3 domain of one heavy chain the amino acid L at position 351 is substituted by Y and the amino acid Y at position 407 is substituted by A, and in the CH3 domain of the other heavy chain the amino acid T at position 366 is substituted by V and the amino acid K at position 409 is substituted by F (numbering according to Kabat EU index). In another embodiment of the multispecific antibody, in the CH3 domain of one heavy chain the amino acid Y at position 407 is substituted by A, and in the CH3 domain of the other heavy chain the amino acid T at position 366 is substituted by A and the amino acid K at position 409 is substituted by F (numbering according to Kabat EU index). In the last aforementioned embodiment, in the CH3 domain of the other heavy chain the amino acid K at position 392 is substituted by E, the amino acid T at position 411 is substituted by E, the amino acid D at position 399 is substituted by R and the amino acid S at position 400 is substituted by R (numbering according to Kabat EU index).

In one embodiment the approach described in WO 2011/143545 is used to support heterodimerization of the first heavy chain and the second heavy chain of the multispecific antibody. In one embodiment amino acid modifications in the CH3 domains of both heavy chains are introduced at positions 368 and/or 409 (numbering according to Kabat EU index).

In one embodiment the approach described in WO 2011/090762 is used to support heterodimerization of the first heavy chain and the second heavy chain of the multispecific antibody. WO 2011/090762 relates to amino acid modifications according to the "knob-into-hole" (KiH) technology. In one embodiment in the CH3 domain of one heavy chain the amino acid T at position 366 is substituted by W, and in the CH3 domain of the other heavy chain the amino acid Y at position 407 is substituted by A (numbering according to Kabat EU index). In another embodiment in the CH3 domain of one heavy chain the amino acid T at position 366 is substituted by Y, and in the CH3 domain of the other heavy chain the amino acid Y at position 407 is substituted by T (numbering according to Kabat EU index).

In one embodiment the approach described in WO 2011/090762 is used to support heterodimerization of the first heavy chain and the second heavy chain of the multispecific antibody, which is of IgG2 isotype.

In one embodiment the approach described in WO 2009/089004 is used to support heterodimerization of the first heavy chain and the second heavy chain of the multispecific antibody. In one embodiment in the CH3 domain of one heavy chain the amino acid K or N at position 392 is substituted by a negatively charged amino acid (in one embodiment by E or D, in one preferred embodiment by D), and in the CH3 domain of the other heavy chain the amino acid D at position 399 the amino acid E or D at position 356 or the amino acid E at position 357 is substituted by a positively charged amino acid (in one embodiment K or R, in one preferred embodiment by K, in one preferred embodiment the amino acids at positions 399 or 356 are substituted by K) (numbering according to Kabat EU index). In one further embodiment, in addition to the aforementioned substitutions, in the CH3 domain of the one heavy chain the amino acid K or R at position 409 is substituted by a negatively charged amino acid (in one embodiment by E or D, in one preferred embodiment by D) (numbering according to Kabat EU index). In one even further embodiment, in addition to or alternatively to the aforementioned substitutions, in the CH3 domain of the one heavy chain the amino acid K at position 439 and/or the amino acid K at position 370 is substituted independently from each other by a negatively charged amino acid (in one embodiment by E or D, in one preferred embodiment by D) (numbering according to Kabat EU index).

In one embodiment the approach described in WO 2007/147901 is used to support heterodimerization of the first heavy chain and the second heavy chain of the multispecific antibody. In one embodiment in the CH3 domain of one heavy chain the amino acid K at position 253 is substituted by E, the amino acid D at position 282 is substituted by K and the amino acid K at position 322 is substituted by D, and in the CH3 domain of the other heavy chain the amino acid D at position 239 is substituted by K, the amino acid E at position 240 is substituted by K and the amino acid K at position 292 is substituted by D (numbering according to Kabat EU index).

In one embodiment the approach described in WO 2007/110205 is used to support heterodimerization of the first heavy chain and the second heavy chain of the multispecific antibody In one embodiment of all aspects and embodiments as reported herein the multispecific antibody is a bispecific antibody or a trispecific antibody. In one preferred embodiment the multispecific antibody is a bispecific antibody.

In one embodiment of all aspects as reported herein, the antibody is a bivalent or trivalent antibody. In one embodiment the antibody is a bivalent antibody.

In one embodiment of all aspects as reported herein, the multispecific antibody has a constant domain structure of an IgG type antibody. In one further embodiment of all aspects as reported herein, the multispecific antibody is of human subclass IgG1, or of human subclass IgG1 with the mutations L234A and L235A. In one further embodiment of all aspects as reported herein, the multispecific antibody is of human subclass IgG2. In one further embodiment of all aspects as reported herein, the multispecific antibody is of human subclass IgG3. In one further embodiment of all aspects as reported herein, the multispecific antibody is of human subclass IgG4, or of human subclass IgG4 with the additional mutation S228P. In one further embodiment of all aspects as reported herein, the multispecific antibody is of human subclass IgG1, or of human subclass IgG4. In one further embodiment of all aspects as reported herein, the multispecific antibody is of human subclass IgG1 with the mutations L234A and L235A (numbering according to Kabat EU index). In one further embodiment of all aspects as reported herein, the multispecific antibody is of human subclass IgG1 with the mutations L234A, L235A and P329G (numbering according to Kabat EU index). In one further embodiment of all aspects as reported herein, the multispecific antibody is of human subclass IgG4 with the mutations S228P and L235E (numbering according to Kabat EU index). In one further embodiment of all aspects as reported herein, the multispecific antibody is of human subclass IgG4 with the mutations S228P, L235E and P329G (numbering according to Kabat EU index).

The antibody as reported herein is in one embodiment of human subclass IgG1 with mutations PVA236, L234A/L235A, and/or GLPSS331 (numbering according to EU index of Kabat), or of subclass IgG4. In a further embodiment, the antibody is of any IgG class, in one embodiment of the subclass IgG1 or IgG4, containing at least one mutation in E233, L234, L235, G236, D270, N297, E318, K320, K322, A327, A330, P331 and/or P329 (numbering according to EU index of Kabat). It is further in one embodiment that the antibody is of the IgG4 subclass and contains the mutation S228P, or the mutations S228P and L235E (Angal, S., et al., Mol. Immunol. 30 (1993) 105-108) (numbering according to EU index of Kabat).

The C-terminus of the heavy chain of the antibody as reported herein can be a complete C-terminus ending with the amino acid residues PGK. The C-terminus of the heavy chain can be a shortened C-terminus in which one or two of the C-terminal amino acid residues have been removed. In one preferred embodiment the C-terminus of the heavy chain is a shortened C-terminus ending PG.

In one embodiment of all aspects as reported herein, an antibody comprising a heavy chain including a C-terminal CH3 domain as specified herein, comprises the C-terminal glycine-lysine dipeptide (G446 and K447, numbering according to Kabat EU index). In one embodiment of all aspects as reported herein, an antibody comprising a heavy chain including a C-terminal CH3 domain, as specified herein, comprises a C-terminal glycine residue (G446, numbering according to Kabat EU index).

The following examples, sequences and figures are provided to aid the understanding of the present invention, the true scope of which is set forth in the appended claims. It is understood that modifications can be made in the procedures set forth without departing from the spirit of the invention.

DESCRIPTION OF THE FIGURES

FIG. 2A: PD1-CLIP; FIG. 2B: PD1-SNAP; FIG. 2C: Tim3-CLIP; FIG. 2D: Tim3-SNAP.

- FIG. 4A: 1+1 format bispecific antibodies (antibodies PD1-Tim3-0389 and PD1-Tim3-0168) and 2+2 format bispecific antibodies (antibodies PD1-Tim3-0358 and PD1-Tim3-0359);
- FIG. 4B: bispecific antibodies PD1-Tim3-0476 and PD1-Tim3-0477.

MATERIALS & GENERAL METHODS

Figure 1:
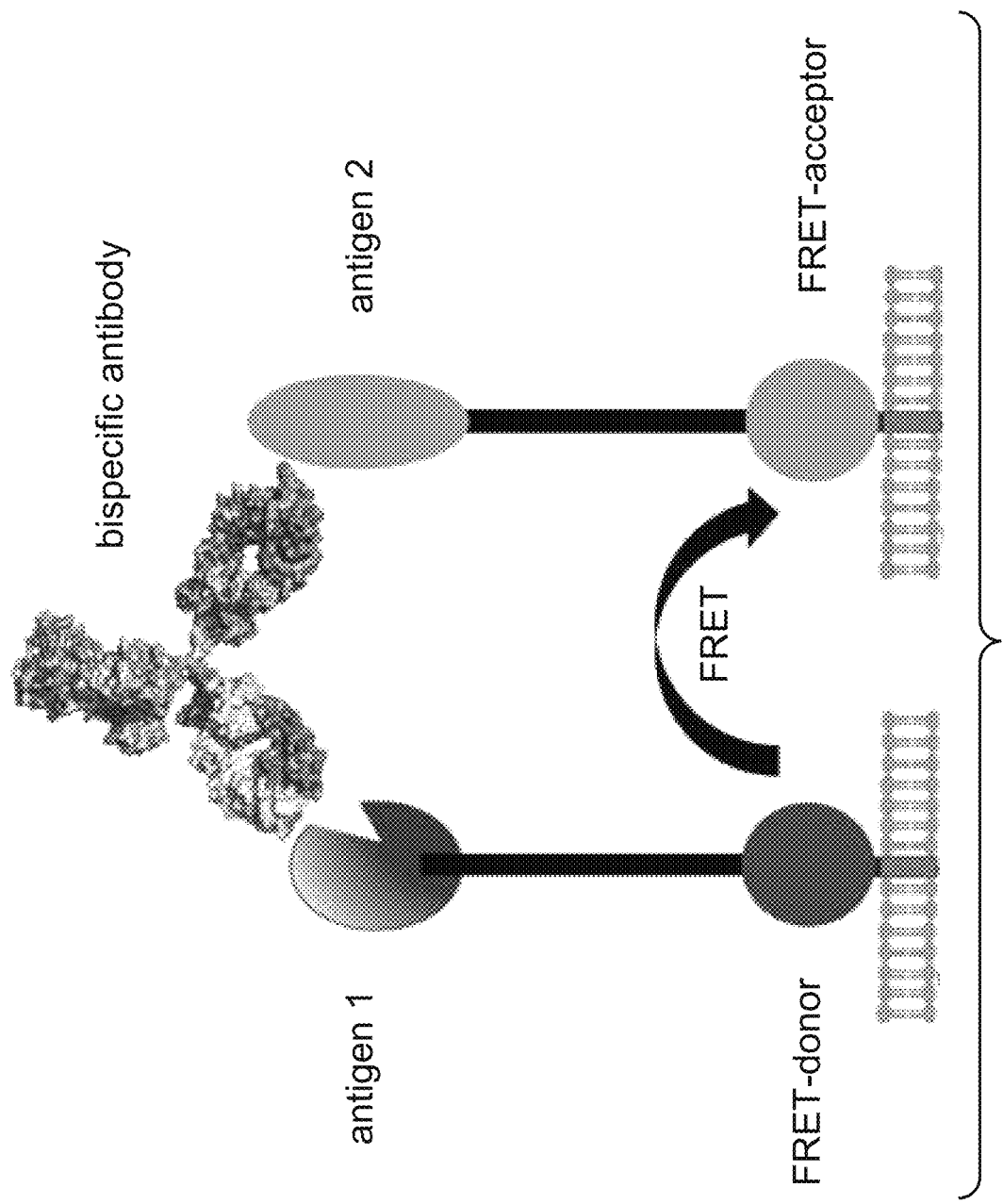
FIG. 1: Scheme of FRET assay as reported herein for FRET induction between FRET-donor and -acceptor after simultaneous binding of bispecific antibodies to recombinant cells presenting the antigens/targets of the bispecific antibody.
Figure 2A:
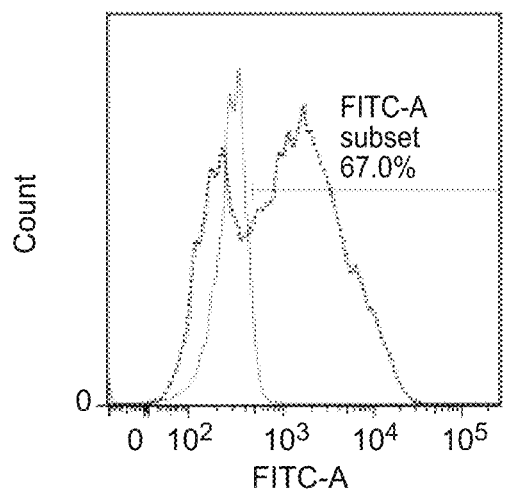
FIG. 2A-2D: FACS results for PD-1 or Tim3 expressing cells (single transfected)
Figure 2B:
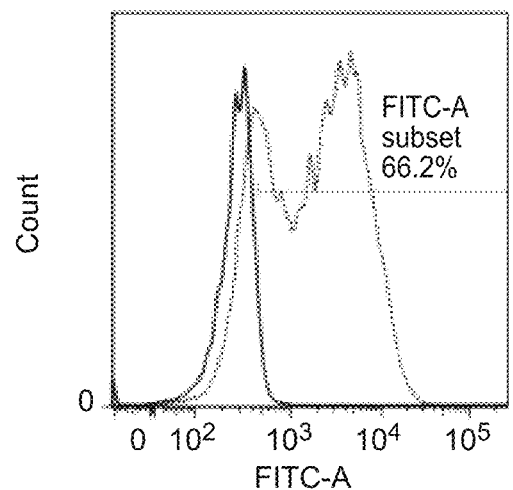
Figure 2C:
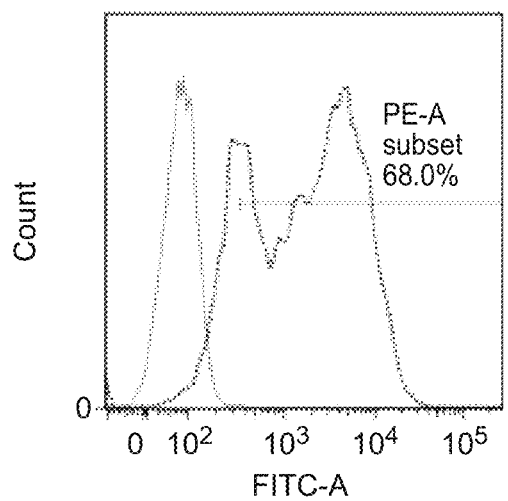
Figure 2D:
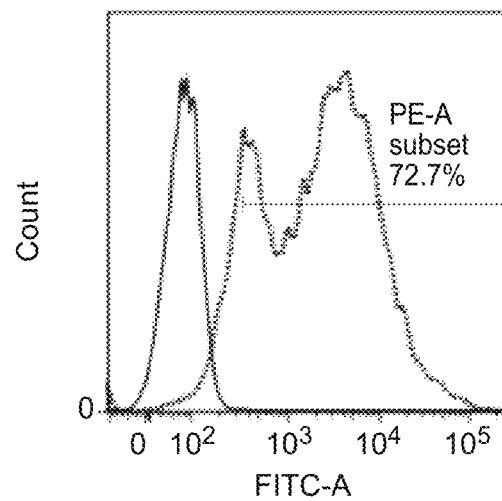

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to numbering according to Kabat (Kabat, E. A., et al., Sequences of Proteins of Immunological Interest, 5th ed., Public Health Service, National Institutes of Health, Bethesda, Md. (1991)).

Recombinant DNA Techniques

Standard methods were used to manipulate DNA as described in Sambrook, J. et al., Molecular Cloning: A laboratory manual; Cold Spring Harbor Laboratory Press, Cold Spring Harbor, N.Y., 1989. The molecular biological reagents were used according to the manufacturer's instructions.

Gene Synthesis

Desired gene segments were prepared from oligonucleotides made by chemical synthesis. The long gene segments, which were flanked by singular restriction endonuclease cleavage sites, were assembled by annealing and ligating oligonucleotides including PCR amplification and subsequently cloned via the indicated restriction sites. The DNA sequences of the subcloned gene fragments were confirmed by DNA sequencing. Gene synthesis fragments were ordered according to given specifications at Geneart (Regensburg, Germany).

DNA Sequence Determination

DNA sequences were determined by double strand sequencing performed at MediGenomix GmbH (Martinsried, Germany) or SequiServe GmbH (Vaterstetten, Germany).

DNA and Protein Sequence Analysis and Sequence Data Management

The GCG's (Genetics Computer Group, Madison, Wis.) software package version 10.2 and Infomax's Vector NT1 Advance suite version 8.0 was used for sequence creation, mapping, analysis, annotation and illustration.

Expression Vectors

For the expression of the described bispecific antibodies, expression plasmids for transient expression (e.g. in HEK293 cells) based either on a cDNA organization with or without a CMV-intron A promoter or on a genomic organization with a CMV promoter can be applied.

Beside the Antibody Expression Cassette the Vectors Contain:

an origin of replication which allows replication of this plasmid in E. coli, and
a ß-lactamase gene which confers ampicillin resistance in E. coli.

The Transcription Unit of the Antibody Gene is Composed of the Following Elements:

unique restriction site(s) at the 5' end
the immediate early enhancer and promoter from the human cytomegalovirus,
the intron A sequence in the case of cDNA organization,
a 5'-untranslated region derived from a human antibody gene,
an immunoglobulin heavy chain signal sequence,
the respective antibody chain encoding nucleic acid either as cDNA or with genomic exon-intron organization,
a 3' untranslated region with a polyadenylation signal sequence, and
unique restriction site(s) at the 3' end.

The fusion genes encoding the antibody chains are generated by PCR and/or gene synthesis and assembled by known recombinant methods and techniques by connection of the according nucleic acid segments e.g. using unique restriction sites in the respective vectors. The subcloned nucleic acid sequences are verified by DNA sequencing. For transient transfections larger quantities of the plasmids are prepared by plasmid preparation from transformed E. coli cultures (Nucleobond AX, Macherey-Nagel).

For all constructs knob-into-hole heterodimerization technology was used with a typical knob (T366W) substitution in the first CH3 domain and the corresponding hole substitutions (T366S, L368A and Y407V) in the second CH3 domain (as well as two additional introduced cysteine residues S354C/Y349'C) (contained in the respective corresponding heavy chain (HC) sequences depicted above).

Cell Culture Techniques

Standard cell culture techniques as described in Current Protocols in Cell Biology (2000), Bonifacino, J. S., Dasso, M., Harford, J. B., Lippincott-Schwartz, J. and Yamada, K. M. (eds.), John Wiley & Sons, Inc., are used.

Transient Transfections in HEK293 System

The bispecific antibodies are produced by transient expression. Therefore a transfection with the respective plasmids using the HEK293 system (Invitrogen) according to the manufacturer's instruction is done. Briefly, HEK293 cells (Invitrogen) growing in suspension either in a shake flask or in a stirred fermenter in serum-free FreeStyle™ 293 expression medium (Invitrogen) are transfected with a mix of the respective expression plasmids and 293Fectin™ or fectin (Invitrogen). For 2 L shake flask (Corning) HEK293 cells are seeded at a density of $1.0*10^6$ cells/mL in 600 mL and incubated at 120 rpm, 8% $CO_2$. On the next day the cells are transfected at a cell density of approx. $1.5*10^6$ cells/mL with approx. 42 mL of a mixture of A) 20 mL Opti-MEM medium (Invitrogen) comprising 600 µg total plasmid DNA (1 µg/mL) and B) 20 ml Opti-MEM medium supplemented with 1.2 mL 293 fectin or fectin (2 µl/mL). According to the glucose consumption glucose solution is added during the course of the fermentation. The supernatant containing the secreted antibody is harvested after 5-10 days and antibodies are either directly purified from the supernatant or the supernatant is frozen and stored.

The relative plasmid ratio of 1:1:1:1 for 1+1 CrossMab or 1:1:1 for 2+2 CrossMab was used for the co-transfection of LC, HC, crossed LC and crossed HC plasmids.

Protein Determination

The protein concentration of purified antibodies and derivatives was determined by determining the optical density (OD) at 280 nm, using the molar extinction coefficient calculated on the basis of the amino acid sequence according to Pace, et al., Protein Science 4 (1995) 2411-1423.

Antibody Concentration Determination in Supernatants

The concentration of antibodies and derivatives in cell culture supernatants was estimated by immunoprecipitation with protein A agarose-beads (Roche Diagnostics GmbH, Mannheim, Germany). Therefore, 60 µL protein A Agarose beads were washed three times in TBS-NP40 (50 mM Tris buffer, pH 7.5, supplemented with 150 mM NaCl and 1% Nonidet-P40). Subsequently, 1-15 mL cell culture supernatant was applied to the protein A Agarose beads pre-equilibrated in TBS-NP40. After incubation for at 1 hour at room temperature the beads were washed on an Ultrafree-MC-filter column (Amicon) once with 0.5 mL TBS-NP40, twice with 0.5 mL 2× phosphate buffered saline (2×PBS, Roche Diagnostics GmbH, Mannheim, Germany) and briefly four times with 0.5 mL 100 mM Na-citrate buffer (pH 5.0).

Bound antibody was eluted by addition of 35 μl NuPAGE® LDS sample buffer (Invitrogen). Half of the sample was combined with NuPAGE® sample reducing agent or left unreduced, respectively, and heated for 10 min at 70° C. Consequently, 5-30 μl were applied to a 4-12% NuPAGE® Bis-Tris SDS-PAGE gel (Invitrogen) (with MOPS buffer for non-reduced SDS-PAGE and MES buffer with NuPAGE® antioxidant running buffer additive (Invitrogen) for reduced SDS-PAGE) and stained with Coomassie Blue.

The concentration of the antibodies in cell culture supernatants was quantitatively measured by affinity HPLC chromatography. Briefly, cell culture supernatants containing antibodies that bind to protein A were applied to an Applied Biosystems Poros A/20 column in 200 mM $KH_2PO_4$, 100 mM sodium citrate, pH 7.4 and eluted with 200 mM NaCl, 100 mM citric acid, pH 2.5 on an Agilent HPLC 1100 system. The eluted antibody was quantified by UV absorbance and integration of peak areas. A purified standard IgG1 antibody served as a standard.

Alternatively, the concentration of antibodies and derivatives in cell culture supernatants was measured by Sandwich-IgG-ELISA. Briefly, StreptaWell High Bind Streptavidin A-96 well microtiter plates (Roche Diagnostics GmbH, Mannheim, Germany) were coated with 100 μL/well biotinylated anti-human IgG capture molecule F(ab')2<h-Fcγ>BI (Dianova) at 0.1 μg/mL for 1 hour at room temperature or alternatively overnight at 4° C. and subsequently washed three times with 200 μL/well PBS, 0.05% Tween (PBST, Sigma). Thereafter, 100 μL/well of a dilution series in PBS (Sigma) of the respective antibody containing cell culture supernatants was added to the wells and incubated for 1-2 hour on a shaker at room temperature. The wells were washed three times with 200 μL/well PBST and bound antibody was detected with 100 μl F(ab')2<hFcγ>POD (Dianova) at 0.1 μg/mL as the detection antibody by incubation for 1-2 hours on a shaker at room temperature. Unbound detection antibody was removed by washing three times with 200 μL/well PBST. The bound detection antibody was detected by addition of 100 μL ABTS/well followed by incubation. Determination of absorbance was performed on a Tecan Fluor Spectrometer at a measurement wavelength of 405 nm (reference wavelength 492 nm).

Preparative Antibody Purification

Antibodies were purified from filtered cell culture supernatants referring to standard protocols. In brief, antibodies were applied to a protein A Sepharose column (GE healthcare) and washed with PBS. Elution of antibodies was achieved at pH 2.8 followed by immediate neutralization. Aggregated protein was separated from monomeric antibodies by size exclusion chromatography (Superdex 200, GE Healthcare) in PBS or in 20 mM Histidine buffer comprising 150 mM NaCl (pH 6.0). Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® antioxidant running buffer additive) or MOPS (non-reduced gels) running buffer was used.

CE-SDS

Purity and antibody integrity were analyzed by CE-SDS using microfluidic Labchip technology (PerkinElmer, USA). Therefore, 5 μl of antibody solution was prepared for CE-SDS analysis using the HT Protein Express Reagent Kit according manufacturer's instructions and analyzed on LabChip GXII system using a HT Protein Express Chip. Data were analyzed using LabChip GX Software.

Analytical Size Exclusion Chromatography

Size exclusion chromatography (SEC) for the determination of the aggregation and oligomeric state of antibodies was performed by HPLC chromatography. Briefly, protein A purified antibodies were applied to a Tosoh TSKgel G3000SW column in 300 mM NaCl, 50 mM $KH_2PO_4$/$K_2HPO_4$ buffer (pH 7.5) on an Dionex Ultimate® system (Thermo Fischer Scientific), or to a Superdex 200 column (GE Healthcare) in 2×PBS on a Dionex HPLC-System. The eluted antibody was quantified by UV absorbance and integration of peak areas. BioRad Gel Filtration Standard 151-1901 served as a standard.

Mass Spectrometry

This section describes the characterization of the bispecific antibodies with emphasis on their correct assembly. The expected primary structures were analyzed by electrospray ionization mass spectrometry (ESI-MS) of the deglycosylated intact antibody and in special cases of the deglycosylated/limited LysC digested antibody.

The antibodies were deglycosylated with N-Glycosidase F in a phosphate or Tris buffer at 37° C. for up to 17 h at a protein concentration of 1 mg/ml. The limited LysC (Roche Diagnostics GmbH, Mannheim, Germany) digestions were performed with 100 μg deglycosylated antibody in a Tris buffer (pH 8) at room temperature for 120 hours, or at 37° C. for 40 min, respectively. Prior to mass spectrometry the samples were desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

Example 1

Production and Expression of Multispecific Antibodies which Bind to PD1 and Tim3

Multispecific (bispecific) antibodies which binds to human PD1 and human Tim3 were generated as described in the general methods section by classical molecular biology techniques and were expressed transiently in HEK 293 cells as described above.

Bispecific Antibodies with VH/VL Domain Exchange/Replacement (CrossMAb$^{VH-VL}$) in One Binding Arm (1+1 Bispecific Antibody Format)

The used bispecific 1+1 antibody format is described also in WO 2009/080252. The bispecific antibodies were expressed using expression plasmids containing the nucleic acids encoding the amino acid sequences depicted in the following Table.

TABLE

Amino acid sequences of light chains (LC) and heavy chains (HC) of the bispecific antibodies (1 + 1 CrossMAb$^{VH-VL}$).

| 1 + 1 antibody | HC1 | HC2 | LC1 | LC2 |
|---|---|---|---|---|
| PD1-Tim3-0389 | SEQ ID NO: 01 | SEQ ID NO: 02 | SEQ ID NO: 03 | SEQ ID NO: 04 |
| PD1-Tim3-0168 | SEQ ID NO: 05 | SEQ ID NO: 06 | SEQ ID NO: 07 | SEQ ID NO: 08 |
| PD1-Tim3-0476 | SEQ ID NO: 09 | SEQ ID NO: 10 | SEQ ID NO: 11 | SEQ ID NO: 12 |
| PD1-Tim3-0477 | SEQ ID NO: 13 | SEQ ID NO: 14 | SEQ ID NO: 15 | SEQ ID NO: 16 |
| PD1-Tim3-0166 | SEQ ID NO: 17 | SEQ ID NO: 18 | SEQ ID NO: 19 | SEQ ID NO: 20 |

For all constructs knobs into holes heterodimerization technology was used with a typical knob (T366W) substitution in the first CH3 domain and the corresponding hole substitutions (T366S, L368A and Y410V) in the second CH3 domain (as well as two additional introduced cysteine residues S354C/Y349C) (contained in the respective corresponding heavy chain (HC) sequences depicted above).

Bispecific Antibodies with VH/VL Domain Exchange/Replacement (2+2 CrossMAb$^{VH-VL}$) in two binding arm (2+2 Bispecific Antibody Format)

The used multispecific 2+2 antibody format is described also in WO 2010/145792. The bispecific antibodies were expressed using expression plasmids containing the nucleic acids encoding the amino acid sequences depicted in the following Table.

TABLE

Amino acid sequences of light chains (LC) and heavy chains (HC), of the bispecific antibody (2 + 2 CrossMAb$^{VH-VL}$).

| 2 + 2 antibody | HC | LC1 | LC2 |
|---|---|---|---|
| PD1-Tim3-0358 | SEQ ID NO: 21 | SEQ ID NO: 22 | SEQ ID NO: 23 |
| PD1-Tim3-0359 | SEQ ID NO: 24 | SEQ ID NO: 25 | SEQ ID NO: 26 |
| PD1-Tim3-0321 | SEQ ID NO: 27 | SEQ ID NO: 28 | SEQ ID NO: 29 |

Example 2

Purification and Characterization of Multispecific Antibodies which Bind to PD1 and Tim3

The bispecific antibodies expressed above were purified from the supernatant by a combination of preparative protein A affinity chromatography and preparative size exclusion chromatography. All bispecific antibodies can be produced in good yields and are stable. The obtained products were characterized for identity by mass spectrometry and analytical properties such as purity by SDS-PAGE, monomer content and stability.

Mass Spectrometry

The expected primary structures were analyzed by electrospray ionization mass spectrometry (ESI-MS) of the deglycosylated intact bispecific antibodies and deglycosylated/plasmin digested or alternatively deglycosylated/limited LysC digested bispecific antibody.

The bispecific antibodies were deglycosylated with N-Glycosidase F in a phosphate or Tris buffer at 37° C. for up to 17 h at a protein concentration of 1 mg/ml. The plasmin or limited LysC (Roche Diagnostics GmbH, Mannheim, Germany) digestions were performed with 100 μg deglycosylated bispecific antibody in a Tris buffer (pH 8) at room temperature for 120 hours or at 37° C. for 40 min, respectively. Prior to mass spectrometry the samples were desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

Example 3

FRET Assay for Simultaneous Binding of Bispecific Antibodies to Recombinant Cells General In this example a cell-based TR-FRET assay to determine the simultaneous binding of bispecific antibody formats to two different targets, such as, e.g., receptors, presented on one cell's outer membrane (surface) is described. The Tag-Lite® technology has been chosen as an exemplary FRET method but any other FRET method could be equally chosen. It is a combination of a classical TR-FRET (time-resolved fluorescence resonance energy transfer) and SNAP-tag technology (e.g. New England Biolabs, CISBIO), which allows antigens present on the cell surface to be labeled with a fluorescent donor or acceptor dye.

With this assay format it is possible to demonstrate the simultaneous binding of bispecific antibodies to cells expressing both antigens of the bispecific antibody, in this case PD1 and Tim3 receptors. The antigens are presented as recombinant fusion proteins consisting of the extracellular domains (ECD) of the given receptor and a tag, to which a fluorescence dye can be added. In the presence of an anti-PD1/Tim3 bispecific antibody, which can bind both receptors and, thus, indirectly thereby the FRET-donor and the FRET-acceptor, upon simultaneous binding the two receptors and likewise the FRET-donor and the FRET-acceptor will come into close proximity to allow energy transfer (FRET) (see FIG. 1).

Using an intracellular approach with two bispecific antibodies that work in extracellular approach, resulted in no FRET induction. The background with membrane-permeable dyes, which have to be used in this approach, is pretty high (data not shown).

Generation of Recombinant PD1$^+$Tim3$^+$HEK Cells

Standard methods were used to generate DNA as described in Sambrook et al., Molecular cloning: A laboratory manual; Cold Spring Harbor Laboratory Press, Cold Spring Harbor, N.Y., 1989. For Cloning of PD1 and Tim3 variants SNAP or CLIP was inserted proximal to the respective transmembrane-region of the receptor and cytoplasmatic domain was removed except for 7 amino acid residues and replaced by a Flag-tag.

Transient Transfection

HEK293 cells were co-transfected with transfection reagent 293free (Novagen) and Opti-MEM® I Reduced Serum Media (Life Technologies) in 30 ml culture volume using two plasmids at a time with 15 μg total amount of DNA. Briefly, HEK293 cells were transiently transfected with the following plasmids encoding for a fusion protein consisting of PD1 or Tim3 ECDs, respectively, and a SNAP or CLIP tag, respectively, as described elsewhere:
Plasmids:
a) PD1-SNAP (in 5' to 3' direction):
   nucleic acid encoding human PD1-extracellular domain including the signal peptide (residue 1-170 of SEQ ID NO: 30),
   nucleic acid encoding GGGGS spacer (SEQ ID NO: 31),
   nucleic acid encoding SNAP from pSNAP-tag(T7)2 (without N-terminal methionine residue) which is a mutant form of the human gene for O6-alkylguanine-DNA-alkyltransferase (hAGT). (Compared to wild type hAGT, the SNAP-tag protein contains the mutations C26A, K125A, A127T, R128A, G131K, G132T, M134L, R135S, C150S, N157G, S159E, and is truncated after G182) (SEQ ID NO: 32),
   nucleic acid encoding GGGGS spacer (SEQ ID NO: 31),
   nucleic acid encoding human PD1-transmembrane and cytoplasmic domain (residue 171-191 of SEQ ID NO: 30),
   nucleic acid encoding GGGGS spacer (SEQ ID NO: 31),
   nucleic acid encoding the Flag-tag (DYKDDDDK; SEQ ID NO: 33).
b) Tim3-CLIP (in 5' to 3' direction):
   nucleic acid encoding human Tim3-extracellular domain including the signal peptide (residue 1-202 of SEQ ID NO: 34)
   nucleic acid encoding GGGGS spacer (SEQ ID NO: 31),
   nucleic acid encoding CLIP from pCLIPf (without N-terminal methionine residue), which is a mutant form of the human gene for O6-alkylguanine-DNA-alkyltransferase (hAGT) (SEQ ID NO: 35),
   nucleic acid encoding GGGGS spacer (SEQ ID NO: 31),
   nucleic acid encoding human Tim3 transmembrane and cytoplasmic domain (residue 203-230 of SEQ ID NO: 34)
   nucleic acid encoding GGGGS spacer (SEQ ID NO: 31),
   nucleic acid encoding the Flag-tag (DYKDDDDK; SEQ ID NO: 33).

The combination PD1-CLIP and Tim3-SNAP was also constructed and expressed, and resulted in only low but still detectable FRET signals (data not shown).

Upon transfection, cells were incubated in shaker flasks until final usage for FACS (24-48 hrs. after transfection) or FRET experiments (after 48 hrs.).

Confirmation of PD1 and Tim3 Expression on Transiently Transfected HEK293 Cells (by FACS)

24-48 hrs. after transient transfection of HEK293 cells, the cells were analyzed for PD1 and Tim3 expression: Usually, $1-3 \times 10^5$ single or double transfected cells were stained for 30 min. on ice at 10 µg/ml, washed two times with PBS/2% FCS and analyzed on a FacsCanto II using
   FITC-conjugated anti-human PD1 antibody (Biolegend, Cat. No. 329904, clone EH12.2H7) or phycoerythrin (PE)-conjugated anti-human PD-1 antibody (R&D Systems, Cat. No. FAB1086P),
   and/or
   phycoerythrin (PE)-conjugated anti-human Tim3 antibody (R&Dsystems, Cat. No. FAB2365P, clone 344823).

Figure 3:
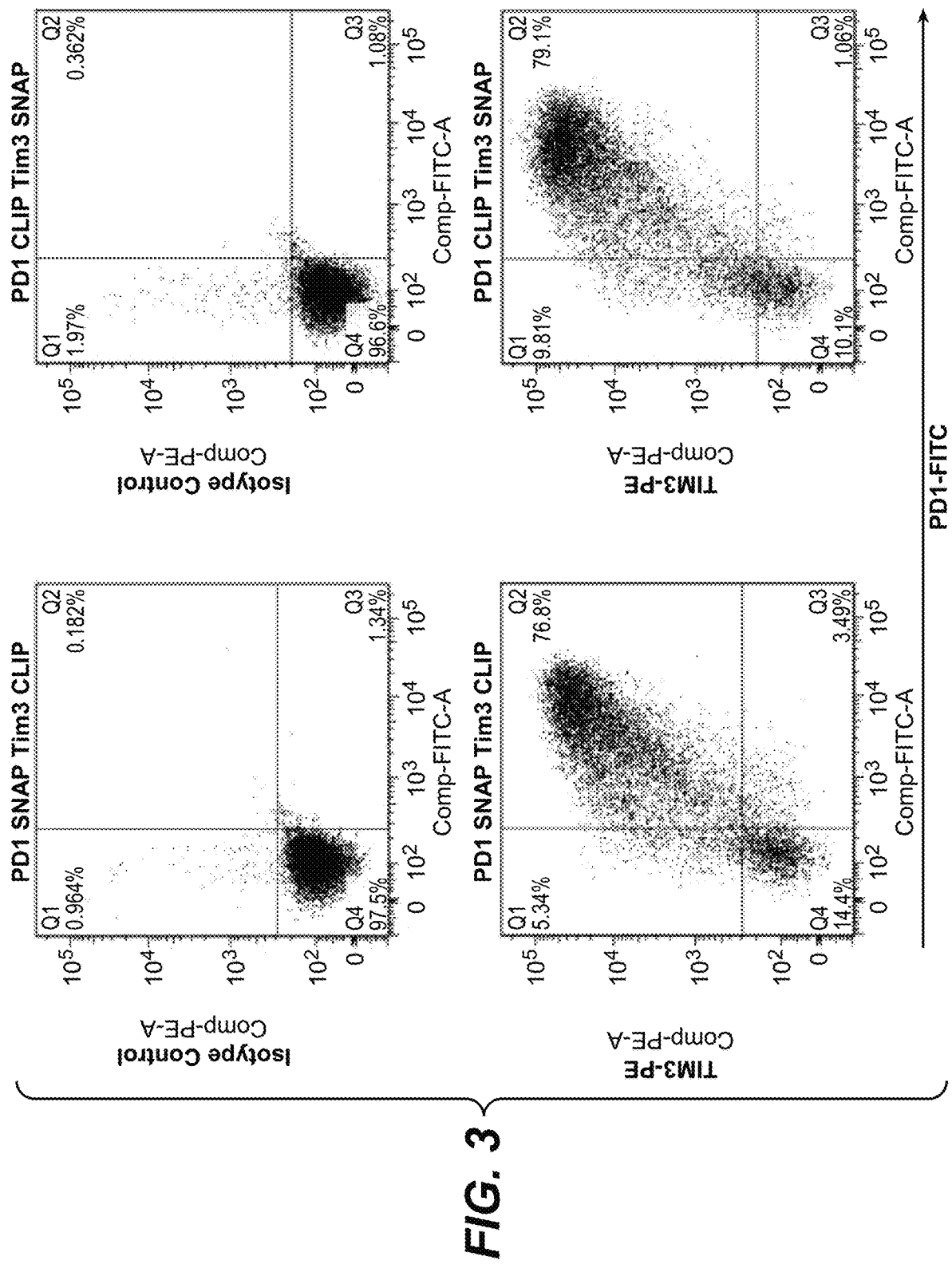
FIG. 3: FACS results for PD-1 and Tim3 expressing cells (double transfected) (lower row of dotplots); staining of respective isotype controls is shown in upper row of dotplots.

The FACS results for the single transfected cells are shown in FIG. 2 and for the double transfected cells are shown in FIG. 3.

Description Cell Labeling and FRET Assay with Anti-PD1/Tim3 Bispecific Antibodies Transfected cells were sedimented and resuspended at a density of $1 \times 10^6$ cells/ml in tag-Lite® buffer (Cisbio). Thereafter, cells were stained with 100 nM SNAP-Lumi4-Tb (Cisbio) and 100 nM CLIP-Red (Cisbio) for one hour at 37° C. in tag-Lite® buffer (Cisbio). After washing and re-suspending in PBS buffer comprising 2% FCS (v/v), about 50.000 cells (in 50 µl volume) were seeded into 96-well flat-bottom white plates (Costar) bevor either control antibody (e.g. a bivalent, monospecific antibody or an isotype control) or bispecific antibody was added to the cells at a final concentration of 0.001-10 nM. After an incubation for one hour at 4° C. or room temperature, time-resolved fluorescence was measured as ratio of the emission signal at 665 nm and 620 nm (665/620 nm ratio) with a BMG Pherastar reader or Tecan Infinite M1000 Pro using standard settings provided by the respective vendor.

Exemplary standard settings were as follows:
Mode Fluorescence Intensity Top
Excitation Wavelength 340 nm
Emission Wavelength 620/665 nm
Excitation Bandwidth 20 nm
Emission Bandwidth 10 nm
Gain 232 Optimal (100%)
Number of Flashes 100
Flash Frequency 100 Hz
Integration Time 500 µs
Lag Time 60 µs
Settle Time 0 ms Optionally, SNAP-Lumi4-Tb and 100 nM CLIP-Red labeled cells were stored at −80° C. or in liquid nitrogen and freshly thawed for FRET experiments.

Alternatively in some cases cross-linking of the parenteral, monovalent or bivalent monospecific monoclonal antibodies via goat anti human Fc-region antibody (20 nM final concentration) could be possible.

To show the specificity of the FRET reaction induced by simultaneous binding of the bispecific antibody, monoclonal IgGs of only one specificity were added for competition.
Results PD1 and Tim3 expressing HEK cells were treated as described above to measure FRET signal upon simultaneous receptor binding via incubation with titrated amounts of different bispecific antibodies (0.12 nM-10 nM).

Figure 4A:
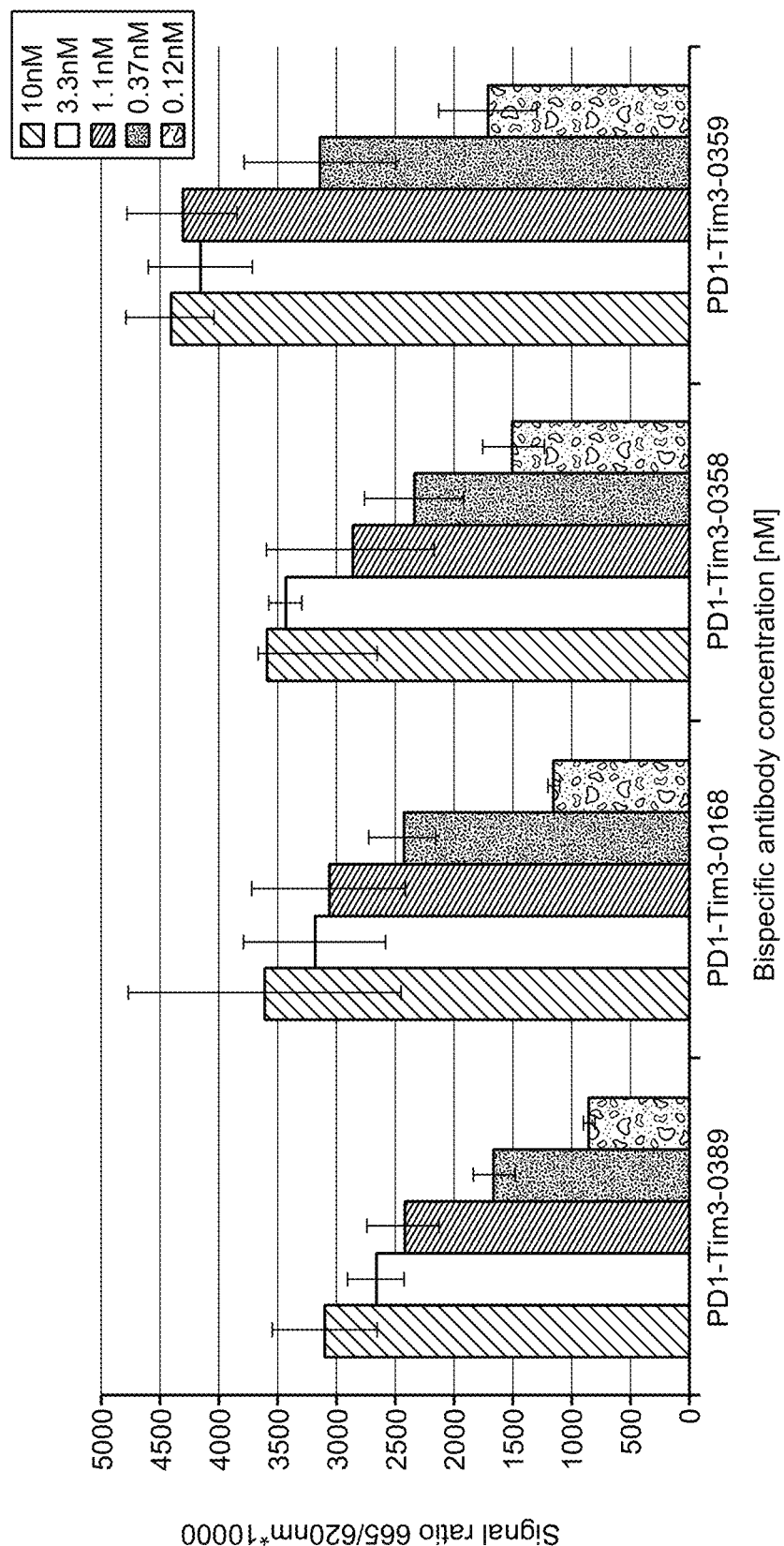
FIG. 4A-4B: Induction of FRET upon treatment/binding of different bispecific anti-PD1/Tim3 antibodies on PD1 and Tim3 expressing cells: time-resolved fluorescence was measured at 665/620 nm using a BMG Pherastar reader (depicted is the mean+/−SD of the FRET signal [ratio 665/620 nm*10,000], n=3)
Figure 4B:
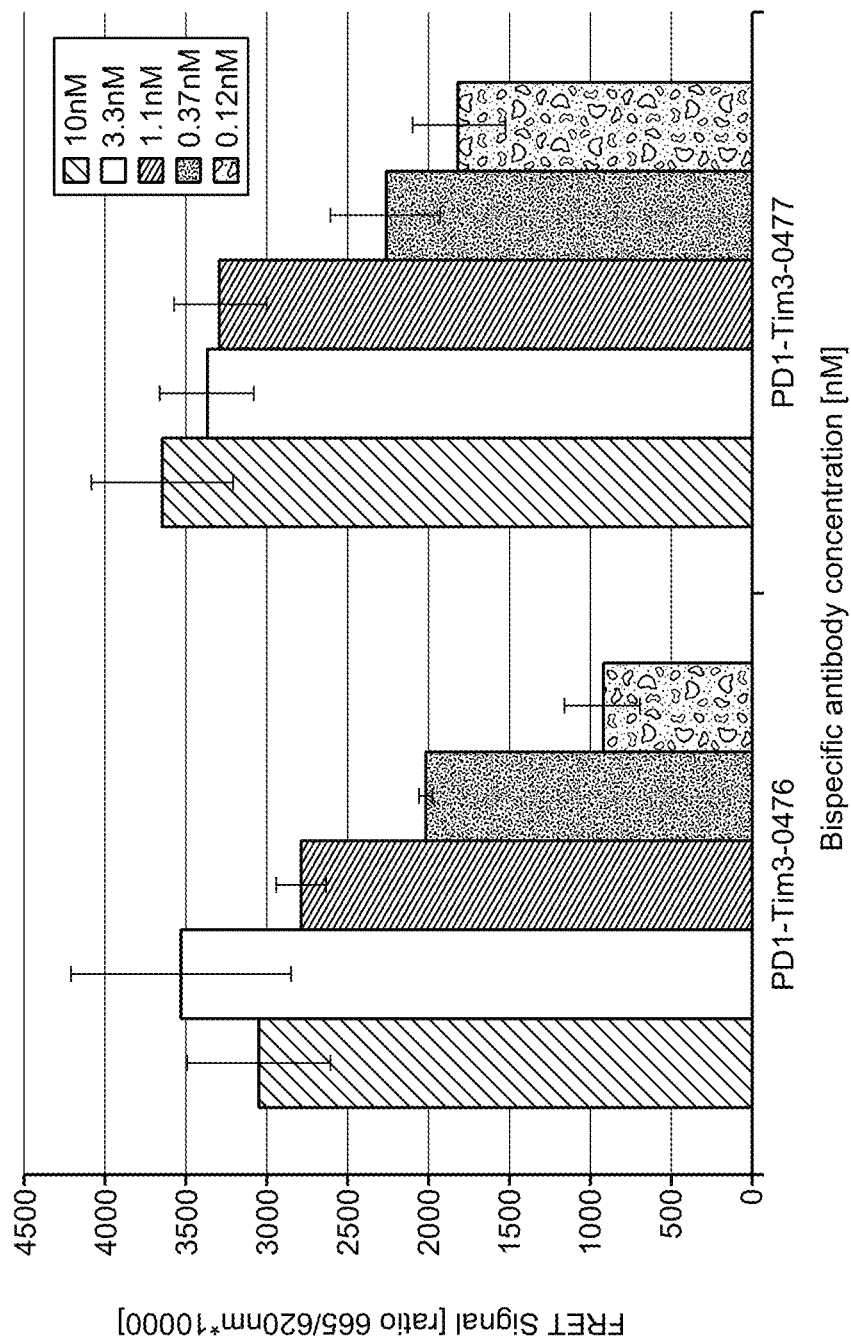

All tested bispecific antibodies induced a FRET signal in PD1/Tim3-expressing cells in a dose-dependent manner. All tested bispecific antibody formats (1+1, 2+2 and 2+1 (data not shown)) were comparable. A comparison of the results obtained with 1+1 format bispecific antibodies (antibodies PD1-Tim3-0389 and PD1-Tim3-0168) and 2+2 format bispecific antibodies (antibodies PD1-Tim3-0358 and PD1-Tim3-0359) is shown in FIG. 4A. Two further bispecific antibodies PD1-Tim3-0476 and PD1-Tim3-0477 were also evaluated for their ability to induce FRET in cells upon treatment. As shown in FIG. 4B both bispecific antibodies induced significant FRET signal in PD1$^+$Tim3$^+$ HEK cells underlining the simultaneous binding in a functional manner.

Figure 5:
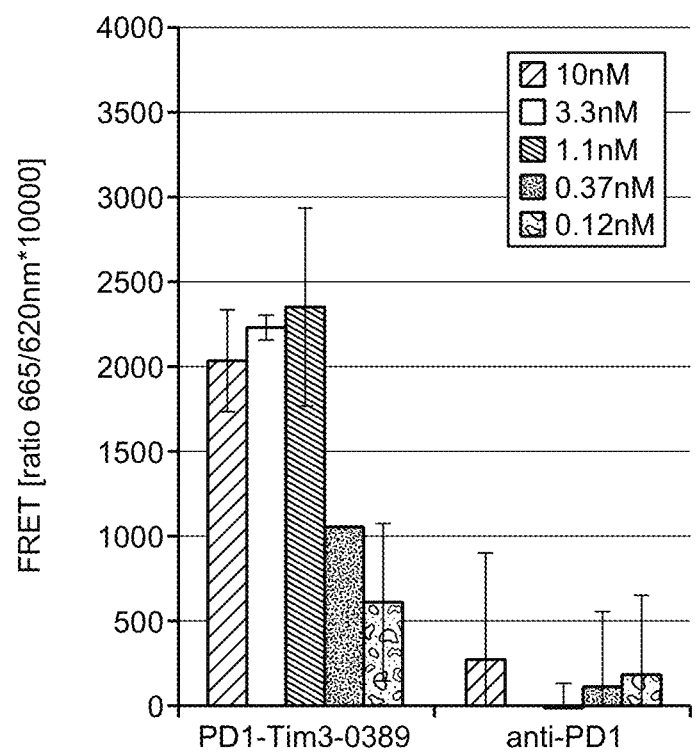
FIG. 5: Induction of FRET upon treatment/binding of a bispecific anti-PD1/Tim3 antibody on PD1 and Tim3 expressing cells: time-resolved fluorescence was measured at 665/620 nm using a BMG Pherastar reader (depicted is the mean+/−SD of the FRET signal [ratio 665/620 nm*10,000], n=3); 1+1 format bispecific antibody PD1-Tim3-0389 and a monospecific, bivalent anti-PD1 antibody were tested—only the bispecific antibody induced FRET.

Likewise as shown in FIG. 5 the FRET assay is not working if only a monospecific, bivalent antibody is added, whereas for a bispecific antibody (antibody PD1-Tim3-0389) a FRET signal could be observed.

Figure 6:
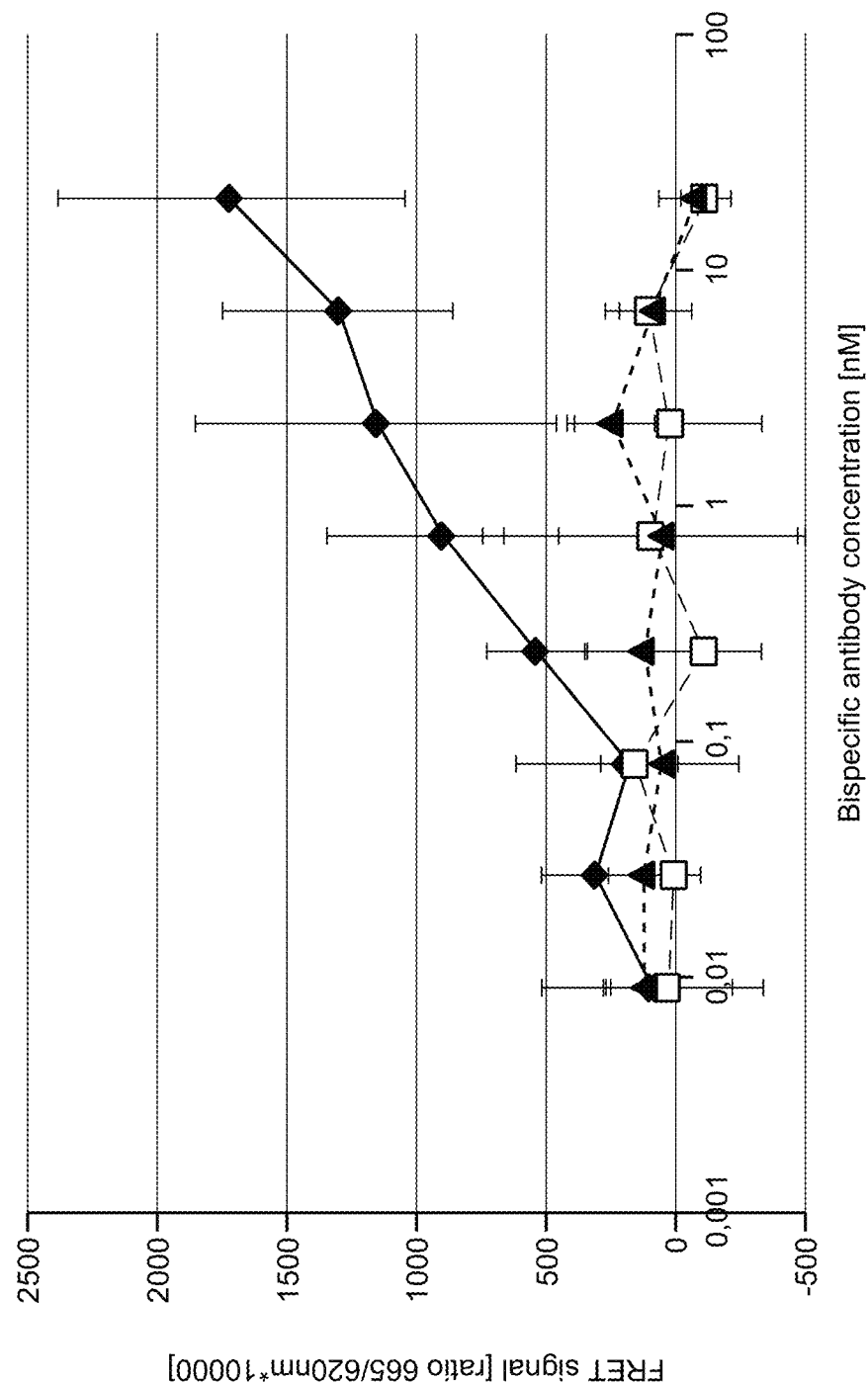
FIG. 6: FRET assay with mono- and bispecific antibody alone or as mixture:
 diamonds: bispecific antibody PD1-Tim3-0168 alone→FRET signal visible;
 square: mixture of bispecific PD1-Tim3-0168 and monospecific anti-PD1 antibody→no FRET signal visible;
 triangle: monospecific, bivalent anti-PD1 monoclonal antibody alone→no FRET signal visible.
Figure 7:
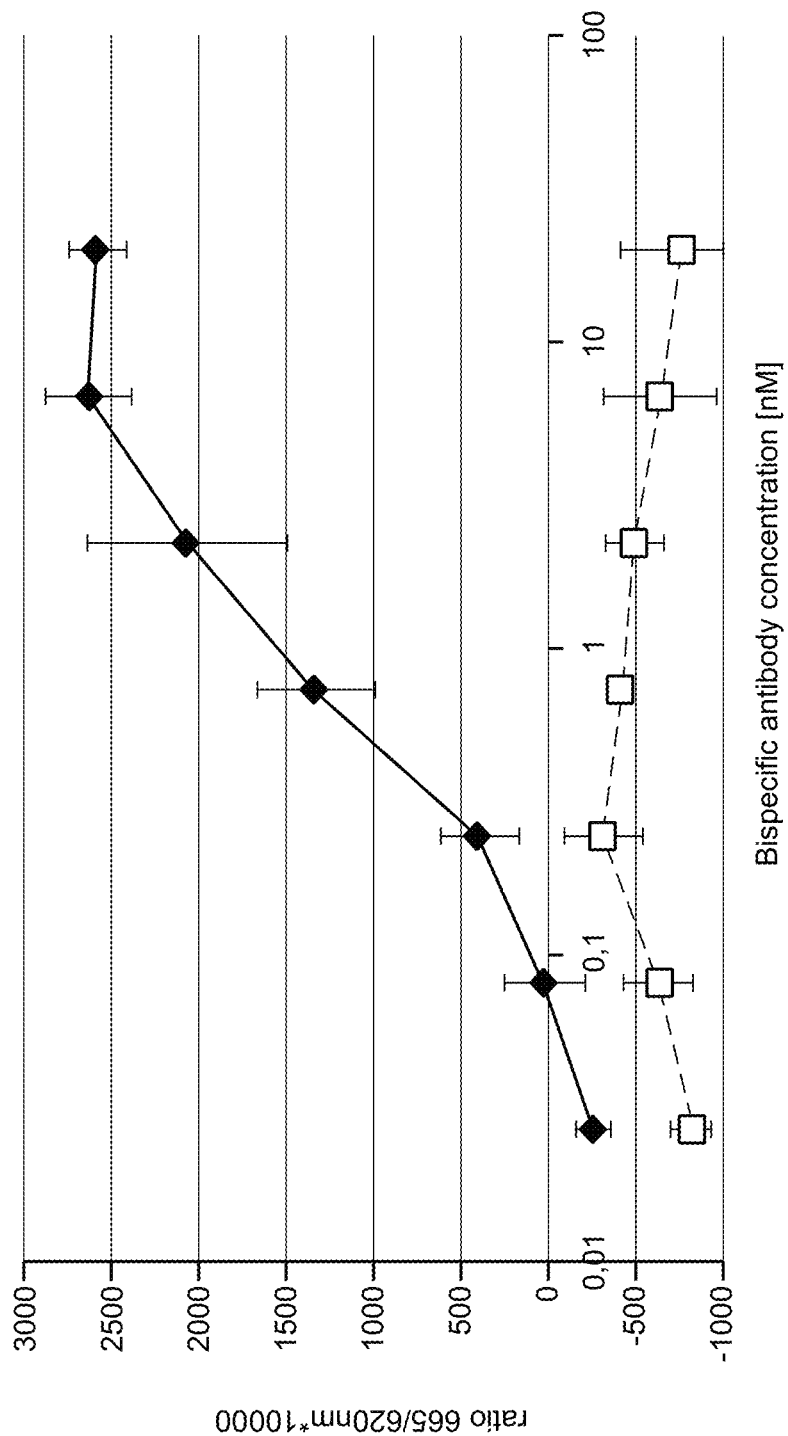
FIG. 7: FRET assay with mono- and bispecific antibody alone or as mixture:
 diamonds: bispecific antibody PD1-Tim3-0168 alone→FRET signal visible;
 square: mixture of bispecific PD1-Tim3-0168 and monospecific anti-Tim3 antibody→no FRET signal visible.

To show the specificity of the FRET signal induced by simultaneous binding of the bispecific antibody, monoclonal IgGs of only one specificity were added for competition. Therefore, PD1 and Tim3 expressing HEK cells as described before were labelled with 100 nM SNAP-Lumi4-Tb and 100 nM CLIP-Red. After washing, labelled cells were incubated with the bispecific anti-PD1/Tim3 antibody PD1-Tim3-0168 at the indicated concentrations of 0.01 nM, 0.05 nM, 0.1 nM, 0.5 nM, 1 nM, 5 nM, 10 nM and 40 nM for one hour at 4° C. before time-resolved fluorescence was measured at 665/620 nm with an BMG Pherastar reader (FIG. 6, diamond). A FRET signal was detected. To underline the specificity of FRET signal after bispecific antibody treatment, a monospecific, bivalent anti-PD1 monoclonal antibody was tested alone (FIG. 6, triangle). No FRET signal was detected. If the monospecific, bivalent anti-PD1 monoclonal antibody and the bispecific anti-PD1/Tim3 antibody were present (80 nM monospecific antibody concentration) no FRET signal was detected (FIG. 6, squares). Likewise no FRET signal was obtained if a bivalent, monospecific anti-Tim3 antibody was added (see FIG. 7).

Example 4

FRET Assay for Determining the Binding Strength

In order to discriminate between the contributions of the two binding sites of a bispecific antibody a competition experiment was performed as outlined below.

To discriminate for the contribution of the PD1 binding site and the Tim3 binding site to the overall interaction a special setting was used. The PD1 binding site has a higher affinity than the Tim3 binding site. The different bispecific antibodies showed similar FRET signal intensity under standard conditions. A difference could be visualized when the PD1 interaction (i.e. the interaction with the higher affinity/lower $K_D$-value) was blocked or at least reduced.

Figure 8:
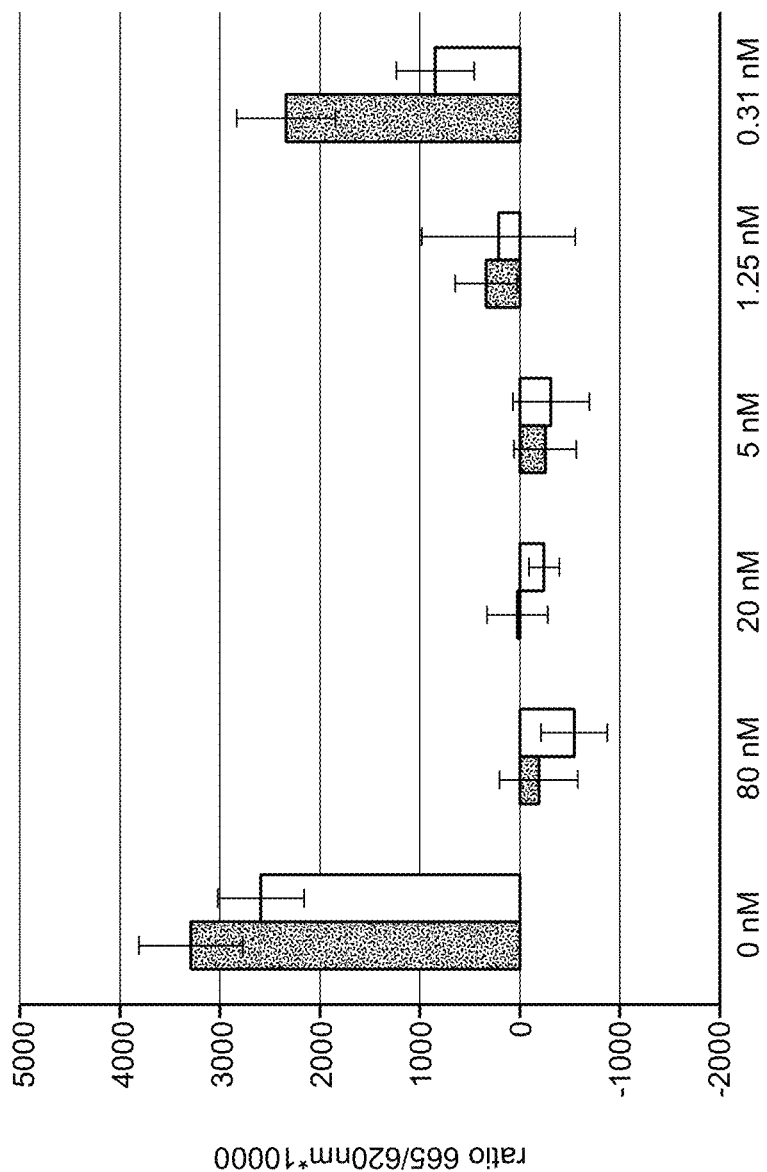
FIG. 8: FRET assay with bispecific antibody and different concentrations of monospecific anti-PD1 antibody→FRET signal dependent on anti-PD1 antibody concentration and Tim3 interaction strength; two different bispecific anti-PD1/Tim3 antibodies were tested: PD1-Tim3-0168 (black) and PD1-Tim3-0389 (grey).

Therefore a monospecific, bivalent anti-PD1 antibody was added at different concentrations (80 nM, 20 nM, 5 nM, 1.25 nM and 0.31 nM) to bispecific anti-PD1/Tim3 antibodies differing in the Tim3 binding site (antibodies PD1-Tim3-0168 and PD1-Tim3-0389). At full PD1 neutralization almost no FRET signal was measured, whereas at lower anti-PD1 antibody concentrations, the FRET signal was restored and a stronger signal was observed with the antibody PD1-Tim3-0168 in which the Tim3 binding site has the higher affinity for Tim3 (see FIG. 8).

The invention claimed is:

1. A method for the determination of the simultaneous binding of a bispecific antibody to a first and a second antigen comprising the following steps:
   a) incubating a cell expressing cell-membrane bound FRET-donor-tagged first antigen and a cell-membrane bound FRET-acceptor-tagged second antigen with the bispecific antibody, and
   b) determining the simultaneous binding of the bispecific antibody by determining the energy transfer from the FRET-donor to the FRET-acceptor.

2. The method according to claim 1, wherein the cell-membrane bound FRET-donor and the cell-membrane bound FRET-acceptor comprise in N- to C-terminal direction: H.sub.2N-antigen—FRET-donor/acceptor—transmembrane domain-COOH.

3. The method according to claim 1, wherein the FRET-donor and/or acceptor is a conjugate of a tag and a FRET-donor-fluorescent dye or a FRET-acceptor-fluorescent dye, respectively.

4. The method according to claim 3, wherein the conjugate is a non-covalent conjugate and the FRET-donor-fluorescent dye and/or the FRET-acceptor-fluorescent dye is a fluorescent-dye conjugated antibody.

5. The method according to claim 3, wherein the conjugate is a covalent conjugate, the tag is an enzyme and the FRET-donor-fluorescent dye and/or the FRET-acceptor-fluorescent dye are fluorescent dye labelled suicide enzyme substrates.

6. The method according to claim 1, wherein i) the FRET-donor or FRET-acceptor is a covalent complex of a SNAP-tag and a benzyl guanine, and ii) the FRET-acceptor or the FRET-donor is a covalent complex of a CLIP-tag and an O2-benzylcytosine, whereby the FRET-donor and the FRET-acceptor are different tags.

7. The method according to claim 1, wherein the bispecific antibody comprises one or two binding sites that specifically bind to the first antigen and one or two binding sites that specifically bind to the second antigen.

8. A method for determining for a bispecific antibody, which comprises a first binding site that specifically binds to a first antigen and a second binding site that specifically binds to a second antigen whereby the two binding sites bind with at least 10 fold difference in binding affinity to their respective antigens, the strength of the binding interaction of the binding site that specifically binds to its antigen with the higher $K_D$-value comprising the following steps: a) incubating a cell expressing cell-membrane bound FRET-donor-tagged first antigen and FRET-acceptor-tagged second antigen with the bispecific antibody and determining the binding of the bispecific antibody by determining the energy transfer from the FRET-donor to the FRET-acceptor, b) repeating step a) in the presence of increasing concentrations of a monospecific antibody comprising the binding site of the bispecific antibody with the lower $K_D$ value, and c) determining the strength of the binding interaction by determining the concentration of the monospecific antibody at which the energy transfer from the FRET-donor to the FRET-acceptor is reduced.

* * * * *